United States Patent
Bieniarz et al.

(10) Patent No.: US 12,123,813 B2
(45) Date of Patent: Oct. 22, 2024

(54) POLYMER STABILIZATION OF CHROMOGEN SOLUTIONS

(71) Applicant: Ventana Medical Systems, Inc., Tucson, AZ (US)

(72) Inventors: Christopher Bieniarz, Tucson, AZ (US); Brian D. Kelly, Tucson, AZ (US); Jerome W. Kosmeder, II, Tucson, AZ (US); Eric J. May, Chandler, AZ (US); Larry Morrison, Oro Valley, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 487 days.

(21) Appl. No.: 16/933,658

(22) Filed: Jul. 20, 2020

(65) Prior Publication Data

US 2020/0348215 A1 Nov. 5, 2020

Related U.S. Application Data

(60) Continuation of application No. 15/483,589, filed on Apr. 10, 2017, now Pat. No. 10,775,281, which is a division of application No. 13/744,504, filed on Jan. 18, 2013, now Pat. No. 9,618,429.

(60) Provisional application No. 61/589,754, filed on Jan. 23, 2012.

(51) Int. Cl.
| | | |
|---|---|---|
| G01N 1/30 | (2006.01) | |
| C12Q 1/28 | (2006.01) | |
| G01N 33/532 | (2006.01) | |
| G01N 33/535 | (2006.01) | |
| G01N 33/543 | (2006.01) | |
| G01N 33/58 | (2006.01) | |

(52) U.S. Cl.
CPC ............ *G01N 1/30* (2013.01); *C12Q 1/28* (2013.01); *G01N 33/532* (2013.01); *G01N 33/535* (2013.01); *G01N 33/54393* (2013.01); *G01N 33/581* (2013.01); *G01N 2001/302* (2013.01)

(58) Field of Classification Search
CPC ...... G01N 1/30; G01N 33/532; G01N 33/535; G01N 33/54393; G01N 33/581; G01N 2001/302
See application file for complete search history.

(56) References Cited

U.S. PATENT DOCUMENTS

| | | |
|---|---|---|
| 4,789,630 A | 12/1988 | Bloch et al. |
| 5,013,646 A | 5/1991 | Woiszwillo |
| 5,045,932 A | 9/1991 | Sharman et al. |
| 5,160,436 A | 11/1992 | Hildenbrand et al. |
| 5,418,138 A | 5/1995 | Miller et al. |
| 5,487,975 A | 1/1996 | Miller et al. |
| 5,804,404 A | 9/1998 | Heras et al. |
| 6,110,687 A | 8/2000 | Nilsen |
| 7,695,929 B2 | 4/2010 | Kosmeder et al. |
| 9,618,429 B2 * | 4/2017 | May ..................... G01N 1/30 |
| 2008/0305497 A1 * | 12/2008 | Kosmeder ........ G01N 33/54353 435/7.1 |
| 2010/0233694 A1 | 9/2010 | Kopf-Sill |
| 2011/0262940 A1 | 10/2011 | Hisamoto et al. |
| 2012/0077211 A1 | 3/2012 | Greenfield et al. |
| 2012/0171668 A1 | 7/2012 | May et al. |
| 2013/0230853 A1 | 9/2013 | Lohse |

FOREIGN PATENT DOCUMENTS

| | | |
|---|---|---|
| EP | 0219286 A2 | 4/1987 |
| JP | H05227995 A | 9/1993 |
| JP | 5227995 B2 | 7/2013 |
| WO | 1991000667 A1 | 1/1991 |
| WO | 2010077870 A2 | 7/2010 |
| WO | 2010094283 A1 | 8/2010 |
| WO | WO 2010/077870 * 8/2010 ........... G01N 33/331 |

OTHER PUBLICATIONS

Sheldon, Use of nonisotopic M13 probes for genetic analysis, Proc Natl. Acad. Sci. USA, vol. 83, pp. 9085-9089, Dec. 1986.

* cited by examiner

*Primary Examiner* — Gailene Gabel
(74) *Attorney, Agent, or Firm* — Charney IP Law LLC; Thomas M. Finetti

(57) ABSTRACT

Disclosed embodiments concern a composition comprising DAB chromogen, and/or derivative thereof, a stabilizer, and polymer capable of preventing or reducing DAB precipitation relative to a composition that does not comprise the polymer. Also disclosed herein is a method for using the disclosed composition and embodiments of a kit.

17 Claims, 7 Drawing Sheets

POLYMER STABILIZATION OF CHROMOGEN SOLUTIONS

CROSS-REFERENCE TO RELATED APPLICATION

This application is a continuation of U.S. patent application Ser. No. 15/483,589 filed on Apr. 10, 2017, which application is a divisional of U.S. patent application Ser. No. 13/744,504, filed Jan. 18, 2013, which claims the benefit of U.S. Provisional Application No. 61/589,754, filed Jan. 23, 2012, the specifications of which are incorporated herein by reference in their entirety.

FIELD

The present disclosure concerns embodiments of a composition, a kit, and embodiments of a method for using such compositions, useful for a tissue staining procedure wherein the composition comprises a diaminobenzidine (DAB) chromogen (and/or derivatives thereof) and a polymer capable of reducing or substantially eliminating chromogen precipitation.

BACKGROUND

Certain commercially available DAB chromogen solutions (e.g. OPTIVIEW® DAB solution, Ventana Medical Systems, Inc. Tucson AZ) are stabilized against oxidation. Sodium metabisulfite, for example, has been used as a stabilizing solution at concentrations that do not significantly inhibit DAB tissue staining. Without being limited to a particular theory of operation, this antioxidant is believed (based on elemental analysis) to form an insoluble DAB hydrogen sulfate salt. This DAB hydrogen sulfate salt has low aqueous solubility and readily precipitates from solution. The proposed process is illustrated below.

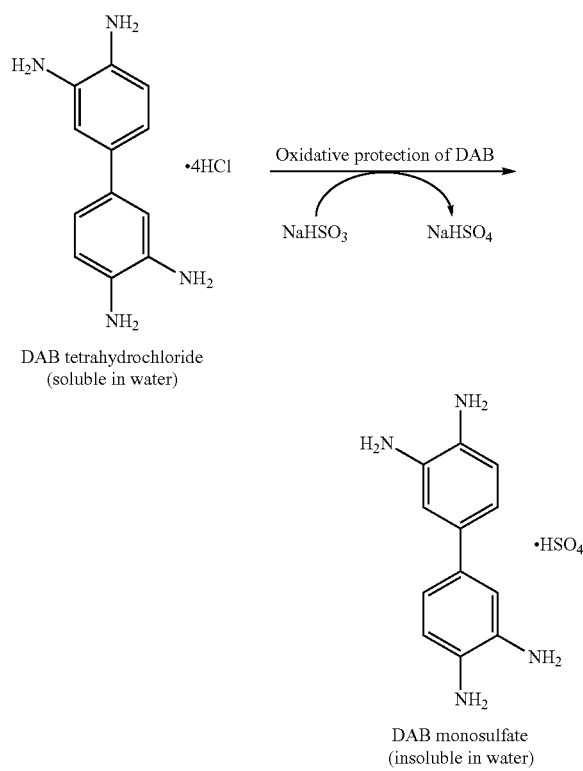

Tetramethyl benzidine chromogens (TMB) are known to associate with dextran sulfate. Dextran sulfate can maintain TMB oxidized products soluble under processes normally used to precipitate TMB chromogen products in solution and also facilitate the TMB deposition in western blotting. [Proc. Natl. Acad. Sci. USA Vol. 83, pp. 9085-9089: "Use of nonisotopic M13 probes for genetic analysis—Application to HLV class II loci", U.S. Pat. No. 4,789,630—"Ionic compounds containing the cationic meriquinone of a benzidine" and U.S. Pat. No. 5,013,646 or WO199100667—"TMB formulation for soluble and precipitable HRP-ELISA"]. There still exists a need in the art, however, to address the problem of DAB-sulfate precipitation prior to DAB oxidation in tissue staining methods.

SUMMARY

The present disclosure concerns a composition, a method for detecting a target within a tissue sample with that composition, and a kit for chromogenic immunohistochemistry. The composition comprises a DAB chromogen at a sufficient concentration and with sufficient stability to be used as a chromogen for the detection of targets in immunohistochemistry. Sufficient stability includes stability in storage such that after extended periods of time (e.g. 6 months, 12 months, 18 months, and 24 months) the chromogen solution can still be used to detect targets in tissue samples without a meaningful decrease in signal compared to the same chromogen solution freshly prepared. Sufficient stability also includes sufficient instability so that when used in detection, sufficient chromogen precipitates to detect the targets in a tissue sample.

In illustrative embodiments, a composition for chromogenic immunohistochemistry includes a solvent, a DAB chromogen, a stabilizer, and a polymer soluble in the solvent. In one embodiment, the polymer reduces DAB precipitation from the solution under accelerated aging conditions relative to a like solution not including the polymer. In another embodiment, the polymer comprises a sulfate functional group, a sulfonate functional group, an amine functional groups, or combinations thereof. In another embodiment, the amine functional groups include a primary amine, a secondary amine, a tertiary amine, or a quaternary amine. In yet another embodiment, the polymer is a polyalkyleneamine polymer. In one embodiment, the polymer is selected from dextran sulfate, polystyrene sulfonate, polyethyleneimine, aminodextran, dextran DEAE, polystyrene sulfonate maleic acid co-polymer, polyvinylsulfonate, poly(2-vinyl-1-methylpyridinium bromide, poly(2-methylacryloxethyltrimethylammonium bromide, poly(acrylamide/2-methylacryloxethyltrimethylammonium bromide, and combinations thereof. In another embodiment, the polymer is a linear or branched polyethyleneimine.

In illustrative embodiments, a composition for chromogenic immunohistochemistry comprises a DAB chromogen and a polymer having a formula selected from

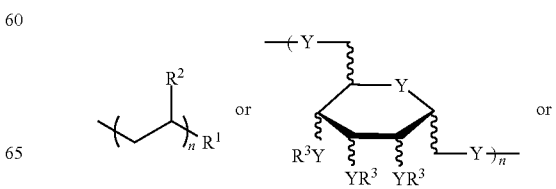

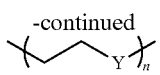

wherein each Y independently is selected from oxygen, sulfur, and $NR^a$ wherein $R^a$ is selected from hydrogen, aliphatic, aryl, heteroaryl, and heteroaliphatic; $R^1$ is selected from aliphatic, aryl, heteroaryl, or a heteroatom-containing moiety, selected from an ester, acid, and amide; $R^2$ is selected from hydrogen, aliphatic, heteroaliphatic, aryl, or heteroaryl; $R^3$ is a polymer functional group selected from a sulfonate, an amine, a carboxyl group, a carboxylate, or combinations thereof; and n ranges from 1 to about 100. In one embodiment, the polymer has a formula of

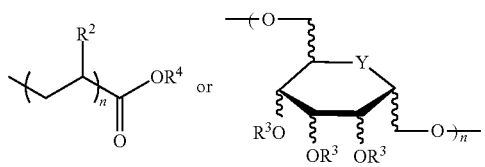

wherein $R^2$ is selected from hydrogen, aliphatic, heteroaliphatic, aryl, or heteroaryl; $R^3$ is a polymer functional group selected from a sulfonate, an amine, a carboxyl group, a carboxylate, or combinations thereof; $R^4$ is selected from hydrogen, aliphatic, and $(CH_2)_q NR^a R^b R^c$ wherein $R^a$, $R^b$, and $R^c$ independently are selected from hydrogen, aliphatic, aryl, and combinations thereof; q ranges from 1 to about 10; and n ranges from 1 to about 100. In another embodiment, the polymer is a co-polymer comprising two or more monomers.

In illustrative embodiments, a composition for chromogenic immunohistochemistry includes an enhancer selected from the group consisting of imidazole, 2-hydroxypyridine, and combinations thereof. In another embodiment, the composition includes the stabilizer sodium metabisulfite. In one embodiment, the polymer reduces DAB precipitation by about 10% to about 100% under accelerated aging conditions relative to the composition that does not include the polymer, determined by either HPLC in an accelerated aging study at 45° C. or by polymer screening using $KHSO_4$. In another embodiment, the polymer reduces DAB precipitation under accelerated aging conditions relative to the composition that does not include the polymer while precipitating equivalently to the composition that does not include the polymer under detection conditions. Illustratively, precipitating equivalently includes generating no statistically significant deviation in average observed staining intensity, as determined by a qualified reader, compared to the composition that does not include the polymer. Further illustratively, the polymer is configured to form a complex with the DAB chromogen so as to maintain solubility of the DAB chromogen in the solvent. In one embodiment, the stabilizer and the polymer substantially prevent the DAB chromogen from decomposing and/or being oxidized under storage conditions.

In illustrative embodiments, a composition for chromogenic immunohistochemistry detection includes a DAB chromogen, an enhancer, a stabilizer, and a polymer; wherein the enhancer is imidazole or 2-hydroxypyridine, the stabilizer is sodium metabisulfite or sodium bisulfite, and the polymer is dextran sulfate, polystyrene sulfonate, polyethyleneimine, aminodextran, dextran DEAE, polystyrene sulfonate maleic acid co-polymer, polyvinylsulfonate, poly(2-vinyl-1-methylpyridinium bromide, poly(2-methylacryloxethyltrimethylammonium bromide, or poly(acrylamide/2-methylacryloxethyltrimethylammonium bromide; wherein the detection solution is configured to remain stable under storage conditions so that the polymer complexes the DAB chromogen or a product thereof so as to maintain the amount of the DAB chromogens in the solution; wherein the detection solution is configured so that the DAB precipitates under detection conditions produces a signal suitable for chromogenic immunohistochemistry. In one embodiment, the DAB chromogen is 3,3'-diaminobenzidine, the stabilizer is sodium metabisulfite, and the polymer is polyethyleneimine. In another embodiment, the composition comprises about 1 to about 15 mM 3,3'-diaminobenzidine, about 1 to about 20 mM imidazole, about 1 to about 20 mM 2-hydroxypyridine, about 0.1 to about 3 mM sodium metabisulfite and about 0.05% to about 0.5% (w/w) polyethyleneimine.

A method for detecting a target in a tissue sample with a DAB chromogen includes contacting the tissue sample with a specific binding moiety, the specific binding moiety being specific to the target, labeling the specific binding moiety with an enzyme conjugate, contacting the tissue sample with a chromogen solution, the chromogen solution comprising DAB or a derivative thereof, a stabilizer, and a polymer configured to reduce DAB precipitation under storage conditions but maintain precipitation under detection conditions, contacting the tissue sample with an oxidant, wherein a reaction between the oxidant, the chromogen solution, and the enzyme conjugate causes the DAB to deposit proximally to the target, contacting the tissue sample with a counterstain, and detecting the target in the tissue sample by locating the DAB chromogen. In one embodiment, the tissue sample is a formalin-fixed, paraffin-embedded tissue sample. In another embodiment, storage conditions include a sealed storage container not in fluid communication with other reagents and detection conditions include deposited on the tissue sample and in contact with the enzyme. In another embodiment, the specific binding moiety is an antibody or a nucleic acid probe. In yet another embodiment, labeling the specific binding moiety includes detecting a hapten selected from an oxazole, a pyrazole, a thiazole, a nitroaryl compound other than dinitrophenyl, a benzofurazan, a triterpene, a urea, a thiourea, a rotenoid, a coumarin, a cyclolignan, a heterobiaryl, an azo aryl, or a benzodiazepine with an enzyme conjugate including an anti-hapten antibody specific to the hapten. In various embodiments, the hapten is selected from HQ, DIG, DNP, TS, NP, DCC, and biotin. In one embodiment, the enzyme is a peroxidase. For example, the enzyme is horseradish peroxidase. In yet other embodiments, contacting the tissue sample with a chromogen solution comprises adding a first component solution comprising the DAB or derivative thereof, a second component solution comprising the stabilizer, and a third component solution comprising the polymer to the tissue sample to form the chromogen solution while in contact with the tissue sample. In further embodiments, the method includes contacting the tissue sample with a DAB composition as described herein.

In illustrative embodiments, a method of detecting a target in a formalin-fixed, paraffin-embedded tissue sample includes contacting the tissue sample with a haptenylated antibody, contacting the tissue sample with an enzyme conjugate comprising an anti-hapten antibody and horseradish peroxidase, contacting the tissue sample with a chromogen composition, the chromogen composition comprising a DAB chromogen, or derivative thereof, an enhancer selected from imidazole, 2-hydroxypyridine, and combinations thereof; sodium metabisulfite; and a polymer selected from dextran sulfate, polystyrene sulfonate, polyethyleneimine, aminodextran, dextran DEAE, polystyrene sulfonate maleic acid co-polymer, polyvinylsulfonate, poly(2-vinyl-1-methylpyridinium bromide, poly(2-methylacryloxethyltrimethylammonium bromide, poly(acrylamide/2-methylacryloxethyltrimethylammonium bromide, and combinations thereof; contacting the tissue sample with hydrogen peroxidase; contacting the tissue sample with a hematoxylin counterstain, and detecting the target in the tissue sample. In further illustrative embodiments, a kit for chromogenic detection of tissue samples includes a DAB chromogen, an enhancer, a stabilizer, and a polymer capable of reducing or preventing DAB precipitation relative to a composition that does not include the polymer, the DAB chromogen and the polymer packaged in a first dispenser or bottle. In one embodiment, the enhancer is selected from imidazole, 2-hydroxypyridine, and combinations thereof and the stabilizer is sodium metabisulfite. In another embodiment, the kit further includes an enzyme and antibody conjugate packaged in a second dispenser or bottle. In another embodiment, the polymer provides from greater than 10% to about 50% reduction in precipitation as determined by either HPLC in an accelerated aging study at 45° C. or by polymer screening using $KHSO_4$. In another embodiment, the antibody is an anti-hapten antibody and the enzyme is a horseradish peroxidase. In another embodiment, the kit further includes hydrogen peroxide packaged in a third dispenser or bottle. In one embodiment, the polymer is present at a concentration effective to reduce precipitation of the DAB chromogen in the first dispenser or bottle while the concentration is also effective for allowing precipitation upon contacting the DAB chromogen with the enzyme and antibody conjugate and the hydrogen peroxide. Illustratively, allowing precipitation includes generating no statistically significant deviation in average observed staining intensity as determined by a qualified reader compared to a comparative chromogenic detection composition that does not include the polymer.

The foregoing and other objects, features, and advantages of the invention will become more apparent from the following detailed description, which proceeds with reference to the accompanying figures.

DETAILED DESCRIPTION

I. Introduction

Figure 1:
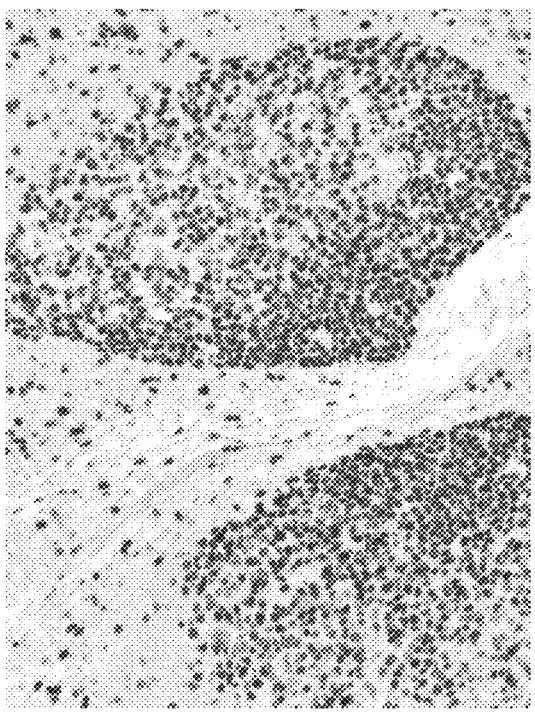
FIG. 1 is an image of a control slide wherein the tonsil tissue sample is stained for Ki67 with a DAB chromogen solution.

The present disclosure concerns a composition comprising a DAB chromogen, and/or derivatives thereof, and a polymer that includes one or more functional groups capable of forming a complex with the chromogen, the counter-ion salt, or the sulfate product of bisulfite oxidation during formulation. An amount of the polymer is used to sufficiently reduce or substantially prevent precipitation of the chromogen. The disclosed composition may be used to increase or improve chromogen deposition during a staining procedure, such as tissue staining. Also disclosed is a method of using the disclosed composition and kits comprising the disclosed composition.

II. Definitions and Abbreviations

Unless otherwise noted, technical terms are used according to conventional usage. Definitions of common terms in molecular biology may be found in Benjamin Lewin, Genes VII, published by Oxford University Press, 2000; Kendrew et al. (eds.), The Encyclopedia of Molecular Biology, published by Blackwell Publishers, 1994); Robert A. Meyers (ed.), Molecular Biology and Biotechnology: a Comprehensive Desk Reference, published by Wiley, John & Sons, Inc., 1995; and George P. Rédei, Encyclopedic Dictionary of Genetics, Genomics, and Proteomics, 2nd Edition, 2003.

The singular forms "a," "an," and "the" refer to one or more than one, unless the context clearly dictates otherwise. For example, the term "comprising a cell" includes single or plural cells and is considered equivalent to the phrase "comprising at least one cell." The term "or" refers to a single element of stated alternative elements or a combination of two or more elements, unless the context clearly indicates otherwise. A wavy line (" ~~~ "), is used to indicate a bond disconnection, and a dashed line (" - - - ") is used to illustrate that a bond may be formed at a particular position.

Although methods and materials similar or equivalent to those described herein can be used to practice or test the disclosed technology, suitable methods and materials are described below. The materials, methods, and examples are illustrative only and not intended to be limiting.

The following explanations of terms and methods are provided to better describe the present disclosure and to guide those of ordinary skill in the art to practice the present disclosure.

Analog, Derivative or Mimetic: An analog is a molecule that differs in chemical structure from a parent compound, for example a homolog (differing by an increment in the chemical structure, such as a difference in the length of an alkyl chain), a molecular fragment, a structure that differs by one or more functional groups, a change in ionization. Structural analogs are often found using quantitative structure activity relationships (QSAR), with techniques such as those disclosed in Remington (*The Science and Practice of Pharmacology*, 19th Edition (1995), chapter 28). A derivative is a biologically active molecule derived from the base structure. A mimetic is a molecule that mimics the activity of another molecule, such as a biologically active molecule. Biologically active molecules can include chemical structures that mimic the biological activities of a compound.

Aryl: A substantially hydrocarbon-based aromatic compound, or a radical thereof (e.g. $C_6H_5$) as a substituent bonded to another group, particularly other organic groups, having a ring structure as exemplified by benzene, naphthalene, phenanthrene, anthracene, etc. This term also encompasses substituted aryl compounds.

Avidin: Any type of protein that specifically binds biotin to the substantial exclusion of other small molecules that might be present in a biological sample. Examples of avidin include avidins that are naturally present in egg white, oilseed protein (e.g., soybean meal), and grain (e.g., corn/maize) and streptavidin, which is a protein of bacterial origin.

Branched: This term refers to a compound and/or functional group comprising one or more units comprising a carbon atom that is bound to at least three other carbon atoms.

Chromogen: A substance capable of conversion to and/or deposition of a colored product, such as a pigment or dye. Certain chromogens are electron donors that, when oxidized, become a colored product. Production of a colored product, and/or the property of becoming insoluble upon chemical conversion, such as by oxidation, make chromogens useful for IHC. Particular examples of chromogenic compounds, without limitation, include 3,3'-diaminobenzidine (DAB), tetramethylbenzidine (TMB), 2,2'-azino-di-[3-ethylbenzothiazoline sulphonate] (ABTS), iodonitrotetrazolium (INT), tetrazolium blue and tetrazolium violet. DAB is a chromogen that produces a brown end product (e.g. through an enzymatic reaction, such as HRP) that is highly insoluble in aqueous solutions.

Conditions sufficient to detect: Any environment that permits the desired activity, for example, that permits a probe to bind a target and the interaction to be detected. For example, such conditions include appropriate temperatures, buffer solutions, and detection means such as microscopes and digital imaging equipment.

Contacting: Placement that allows association between two or more moieties, particularly direct physical association, for example both in solid form and/or in liquid form (for example, the placement of a biological sample, such as a biological sample affixed to a slide, in contact with a composition, such as a solution containing the compositions disclosed herein).

Control: A sample or procedure performed to assess test validity. In one example, a control is a quality control, such as a positive control. For example, a positive control is a procedure or sample, such as a tissue or cell, that is similar to the actual test sample, but which is known from previous experience to give a positive result. A positive control confirms that the basic conditions of the test produce a positive result, even if none of the actual test samples produce such result. In a particular example, a positive control is a sample known by previous testing to contain the suspected antigen. In other examples, a control is a negative control. A negative control is a procedure or test sample known from previous experience to give a negative result. The negative control demonstrates the base-line result obtained when a test does not produce a measurable positive result; often the value of the negative control is treated as a "background" value to be subtracted from the test sample results. In a particular example, a negative control is a reagent that does not include the specific primary antibody. Other examples include calibrator controls, which are samples that contain a known amount of a control antigen. Such calibrator controls have an expected signal intensity, and therefore can be used to correct for inter- or intra-run staining variability.

Detergent or Surfactant: A substance that reduces the surface tension of water. Specifically, a detergent or surfactant is a surface-active agent that concentrates at oil-water interfaces and exerts an emulsifying action. Detergents are classified as anionic, cationic, or nonionic, depending on their mode of chemical action. Nonionic detergents function via a hydrogen-bonding mechanism. Further, surfactants or detergents reduce interfacial tension between two liquids. A surfactant molecule typically has a polar or ionic "head" and a nonpolar hydrocarbon "tail." Upon dissolution in water, the surfactant molecules aggregate and form micelles, in which the nonpolar tails are oriented inward and the polar or ionic heads are oriented outward toward the aqueous environment. The nonpolar tails create a nonpolar "pocket" within the micelle. Nonpolar compounds in the solution are sequestered in the pockets formed by the surfactant molecules, thus allowing the nonpolar compounds to remain mixed within the aqueous solution.

Detect: To determine if an agent (such as a signal or particular antigen, protein or nucleic acid) is present or absent, for example, in a sample. In some examples, this can further include quantification, and/or localization, for example localization within a cell or particular cellular compartment. "Detecting" refers to any method of determining if something exists, or does not exist, such as determining if a target molecule is present in a biological sample. For example, "detecting" can include using a visual or a mechanical device to determine if a sample displays a specific characteristic. In certain examples, detection refers to visually observing a probe bound to a target, or observing that a probe does not bind to a target. For example, light microscopy and other microscopic means are commonly used to detect chromogenic precipitates for methods described here.

Enhanc(e/er/ement/ing): An enhancer or enhancing reagent is any compound or any combination of compounds sufficient to increase the catalytic activity of an enzyme, as compared to the enzyme activity without such compound(s). Enhancer(s) or enhancing reagent(s) can also be defined as a compound or combination of compounds that increase or accelerate the rate of binding an activated conjugate to a receptor site. Enhanc(e/ement/ing) is a process by which the catalytic activity of an enzyme is increased by an enhancer, as compared to a process that does not include such an enhancer. Enhanc(e/ement/ing) can also be defined as increasing or accelerating the rate of binding of an activated conjugate to a receptor site. Enhanc(e/ement/ing) can be measured visually, such as by scoring by a pathologist. In particular embodiments, scores range from greater than 0 to greater than 4, with the higher number indicating better visual detection. More typically, scores range from greater than 0 to about 4++, such as 1, 1.5, 2, 2.5, 3, 3.5, 3.75, 4, 4+, and 4++. In addition, enhanc(e/ement/ing) can be measured by determining the apparent $V_{max}$ of an enzyme. In particular embodiments, the term encompasses apparent $V_{max}$ values (measured as optical density/minute) ranging from greater than 0 mOD/min to about 400 mOD/min, such as about 15 mOD/min, 18 mOD/min, about 20 mOD/min, about 40 mOD/min, about 60 mOD/min, about 80 mOD/min, about 100 mOD/min, about 120 mOD/min, about 140 mOD/min, about 160 mOD/min, about 200 mOD/min, about 250 mOD/min, about 300 mOD/min, about 350 mOD/min, and about 400 mOD/min. More typically, the $V_{max}$ ranges from greater than 0 mOD/min to about 160 mOD/min, such as about 20 mOD/min, about 40 mOD/min, about 60 mOD/min, about 80 mOD/min, about 100 mOD/min, about 120 mOD/min, about 140 mOD/min, and about 160 mOD/min. In addition, enhancement can occur using any concentration of an enhancer greater than 0 mM. Typically, enhancement occurs at enhancer concentrations ranging from great than about 0.01 mM to about 100 mM, such as about 0.01 mM, about 0.02 mM, about 0.05 mM, about 0.10 mM, about 0.20 mM, about 0.50 mM, about 1.0 mM, about 2.0 mM, about 3.0 mM, about 5.0 mM, about 10.0 mM, about 20.0 mM, about 30.0 mM, about 40.0 mM, about 50.0 mM, about 75.0 mM, or about 100.0 mM, such as about 0.01 mM to about 0.10 mM, about 0.05 mM to about 0.50 mM, about 0.4 mM to about 1.0 mM, about 0.5 mM to about 2.0 mM, about 1.0 mM to about 10.0 mM, about 5.0 mM to about 50.0 mM, and about 20.0 mM to about 100.0 mM. Enhanc(e/er/ement/ing), in general and species thereof are disclosed in assignee's co-pending application U.S. Publication No. 2012/0171668, which is incorporated herein by reference.

Fixation: A process which preserves cells and tissue constituents in as close to a life-like state as possible and allows them to undergo preparative procedures without change. Fixation arrests the autolysis and bacterial decomposition processes that begin upon cell death, and stabilizes the cellular and tissue constituents so that they withstand the subsequent stages of tissue processing, such as for IHC. Tissues may be fixed by either perfusion with or submersion in a fixative, such as an aldehyde (such as formaldehyde, paraformaldehyde, glutaraldehyde, and the like). Other fixatives include oxidizing agents (for example, metallic ions and complexes, such as osmium tetroxide and chromic acid), protein-denaturing agents (for example, acetic acid, methanol, and ethanol), fixatives of unknown mechanism (for example, mercuric chloride, acetone, and picric acid), combination reagents (for example, Carnoy's fixative, methacarn, Bouin's fluid, B5 fixative, Rossman's fluid, and Gendre's fluid), microwaves, and miscellaneous (for example, excluded volume fixation and vapour fixation). Additives also may be included in the fixative, such as buffers, detergents, tannic acid, phenol, metal salts (for example, zinc chloride, zinc sulfate, and lithium salts), and lanthanum. The most commonly used fixative in preparing samples for IHC is formaldehyde, generally in the form of a formalin solution (4% formaldehyde in a buffer solution, referred to as 10% buffered formalin).

Hapten: A molecule, typically a small molecule that can combine specifically with an antibody, but typically is substantially incapable of being immunogenic except in combination with a carrier molecule. Exemplary haptens include an oxazole, a pyrazole, a thiazole, a nitroaryl compound other than dinitrophenyl, a benzofurazan, a triterpene, a urea, a thiourea, a rotenoid, a coumarin, a cyclolignan, a heterobiaryl, an azo aryl, or a benzodiazepine. More particularly, the hapten may be 2,4-dinitrophenyl (DNP), biotin, digoxigenin, 5-nitro-3-pyrazolecarbamide (NP), 3-hydroxy-2-quinoxalinecarbamide (HQ), 2-acetamido-4-methyl-5-thiazolesulfonamide (TS), and 4-(diethylamino)azobenene-4'-sulfonamide (DABSYL), or 7-(diethylamino)-2-oxo-2H-chromene-3-carboxyylic acid (DCC).

Immunohistochemistry (IHC): A method of determining the presence or distribution of an antigen in a sample by detecting interaction of the antigen with a specific binding agent or moiety, such as an antibody. A sample including an antigen (such as a target antigen) is incubated with an antibody under conditions permitting antibody-antigen binding. Antibody-antigen binding can be detected by means of a detectable label conjugated to the antibody (direct detection) or by means of a detectable label conjugated to a secondary antibody, which is raised against the primary antibody (e.g., indirect detection). Detectable labels include, but are not limited to, radioactive isotopes, fluorochromes (such as fluorescein derivatives, and rhodamine derivatives), enzymes and chromogenic molecules.

In situ hybridization (ISH): A type of hybridization that uses a labeled complementary DNA or RNA strand (i.e., probe) to localize a specific DNA or RNA sequence in a portion or section of tissue (in situ), or, if the tissue is small enough (e.g., plant seeds, Drosophila embryos), in the entire tissue (whole mount ISH). This is distinct from immunohistochemistry, which localizes proteins in tissue sections. DNA ISH can be used to determine the structure of chromosomes, such as for use in medical diagnostics to assess chromosomal integrity. RNA ISH (hybridization histochemistry) is used to measure and localize mRNAs and other transcripts within tissue sections or whole mounts. For hybridization histochemistry, sample cells and tissues are usually treated to fix the target transcripts in place and to increase access of the probe to the target molecule. As noted above, the probe is either a labeled complementary DNA or a complementary RNA (Riboprobe). The probe hybridizes to the target sequence at elevated temperature, and then the excess probe is washed away (optionally hydrolyzed using RNase in the case of unhybridized, excess RNA probe). Solution parameters, such as temperature, salt and/or detergent concentration, can be manipulated to remove any non-identical interactions (i.e. only exact sequence matches will remain bound). Then, the labeled probe having been labeled effectively, such as with either radio-, fluorescent- or antigen-labeled bases (e.g., digoxigenin), is localized and potentially quantified in the tissue using either autoradiography, fluorescence microscopy or immunohistochemistry, respectively.

Molecule of interest or Target: A molecule for which the presence, location and/or concentration is to be determined. Examples of molecules of interest include proteins and nucleic acid sequences tagged with haptens.

Multiplex, -ed, -ing: Embodiments of the present disclosure allow multiple targets in a sample to be detected substantially simultaneously, or sequentially, as desired, using plural different conjugates. Multiplexing can include identifying and/or quantifying nucleic acids generally, DNA, RNA, peptides, proteins, both individually and in any and all combinations. Multiplexing also can include detecting two or more of a gene, a messenger and a protein in a cell in its anatomic context.

Sample: The term "sample" refers to any liquid, semi-solid or solid substance (or material) in or on which a target can be present. In particular, a sample can be a biological sample or a sample obtained from a biological material. Examples of biological samples include tissue samples and cytology samples. In some examples, the biological sample is obtained from an animal subject, such as a human subject. A biological sample is any solid or fluid sample obtained from, excreted by or secreted by any living organism, including without limitation, single celled organisms, such as bacteria, yeast, protozoans, and amebas among others, multicellular organisms (such as plants or animals, including samples from a healthy or apparently healthy human subject or a human patient affected by a condition or disease to be diagnosed or investigated, such as cancer). For example, a biological sample can be a biological fluid obtained from, for example, blood, plasma, serum, urine, bile, ascites, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease). A biological sample can also be a sample obtained from any organ or tissue (including a biopsy or autopsy specimen, such as a tumor biopsy) or can include a cell (whether a primary cell or cultured cell) or medium conditioned by any cell, tissue or organ. In some examples, a biological sample is a nuclear extract. In some examples, a biological sample is bacterial cytoplasm. In other examples, a sample is a test sample. For example, a test sample is a cell, a tissue or cell pellet section prepared from a biological sample obtained from a subject. In an example, the subject is one that is at risk or has acquired a particular condition or disease.

Specific binding moiety: A member of a specific-binding pair. Specific binding pairs are pairs of molecules that are characterized in that they bind each other to the substantial exclusion of binding to other molecules (for example, specific binding pairs can have a binding constant that is at least $10^3$ M$^{-1}$ greater, $10^4$ M$^{-1}$ greater or $10^5$ M$^{-1}$ greater than a binding constant for either of the two members of the binding pair with other molecules in a biological sample). Particular examples of specific binding moieties include specific binding proteins (for example, antibodies, lectins, avidins such as streptavidins, and protein A), nucleic acids sequences, and protein-nucleic acids. Specific binding moieties can also include the molecules (or portions thereof) that are specifically bound by such specific binding proteins.

Stabilizer: A compound capable of substantially preventing a chromogen from decomposition, precipitation, and/or oxidation. In one embodiment, a stabilizer is an antioxidant, such as sodium metabisulfite.

Tissue: A collection of interconnected cells that perform a similar function within an organism.

III. Chromogen-Polymer Composition

Certain disclosed embodiments concern a composition comprising a chromogen, particularly a DAB chromogen, and/or derivatives thereof, and a polymer capable of forming a complex with the chromogen, the counter-ion salt, or sulfate product of bisulfite oxidation. The disclosed composition may be used in colorimetric procedures, such as tissue staining. A person of ordinary skill in the art will appreciate that a composition useful for a particular protocol may vary from that of a different protocol, and still be within the scope of the composition disclosed herein. Moreover, various optional materials, such as having different reagent concentrations or ratios of reagents amounts, may be included in useful compositions formulated according to the present invention, including, but not limited to, stabilizers, enhancers, counterstains, and/or buffers.

The disclosed composition may be used to increase chromogen deposition, particularly DAB deposition, in staining procedures, such as tissue staining. Table 1 details results obtained from particular working embodiments wherein a base DAB chromogen solution (DAB, imidazole, 2-hydroxypyridine, and sodium metabisulfite) containing a polymer according to the present disclosure was exposed to varying concentrations of potassium hydrogen sulfate ($KHSO_4$).

TABLE 1

| Polymer screening system | | | | |
|---|---|---|---|---|
| 5.5 µmol DAB + 5 wt % Polymer | 0 µmol $KHSO_4$ | 1.37 µmol $KHSO_4$ | 2.75 µmol $KHSO_4$ | 8.0 µmol $KHSO_4$ |
| No Polymer | no ppt | ppt | ppt | ppt |
| 15-20 kDa Dextran | no ppt | no ppt | ppt | ppt |
| 9-20 kDa Dextran Sulfate | no ppt | no ppt | no ppt | no ppt |

Sodium metabisulfite has been used as an antioxidant stabilizer at concentrations that do not significantly inhibit DAB tissue staining. Without being limited to a particular theory of operation, this stabilizer forms an oxidized hydrogen sulfate byproduct which is believed to form insoluble DAB hydrogen sulfate salt precipitate (based on elemental analysis). This DAB hydrogen sulfate salt has a low aqueous solubility and readily precipitates from solution.

HPLC analysis was performed on the polymer-stabilized DAB chromogen to judge heat stress stability (at 45° C.) and each polymer's ability to inhibit DAB sulfate precipitate before and after addition of potassium hydrogen sulfate addition. Samples were analyzed for residual DAB concentration (analytical ultracentrifugation, "AUC") relative to 2-hydroxypyridine (AUC) as an internal standard. The 2-hydroxypyridine concentration was shown to not be influenced by either heat stress or potassium hydrogen sulfate addition. The DAB concentration (AUC) diminished if the DAB tetrahydrochloride formed an insoluble DAB hydrogen sulfate precipitate. This precipitate can be removed from the sample using a pre-column HPLC filter and is, thus, not detectable by HPLC. Thermal stress was shown to expedite DAB oxidation. These byproducts did not accumulate in solution to any substantial concentration and precipitated from solution. Polymers that provided the greatest DAB thermal stability and largest inhibition of DAB sulfate precipitate formation became leading candidates.

Figure 2:
FIG. 2 is an image of a tonsil tissue section stained for Ki67 with a DAB chromogen solution and dextran sulfate (Mw=9-20 kDa, 2 wt %).

As Table 1 indicates, DAB sulfate precipitation was prevented in compositions comprising the chromogen solution and particular embodiments of the disclosed polymer. FIGS. 1 and 2 are images that illustrate the results obtained from particular working embodiments. FIG. 1 is an image of a tissue section stained with a composition comprising solely the DAB chromogen solution and FIG. 2 is an image of a tissue section stained with a composition comprising the DAB chromogen solution and the disclosed polymer (e.g. 2 wt % Dextran Sulfate, Mw=9-20 kDa, no PEG).

A. Chromogens

The disclosed composition may comprise one or more chromogens. Presently disclosed embodiments are particularly directed to forming compositions comprising diaminobenzidine (DAB), and/or derivatives thereof. DAB chromogens, such as 3,3'-diaminobenzidine, have been used for some time for various staining procedures, such as immunoblotting and immunohistochemical staining. The amount of DAB chromogen used for disclosed embodiments can vary, but functionally is used in amounts sufficient to provide an acceptable stained tissue sample, such as an amount of from greater than 0.05 mM to about 100 mM, more typically from greater than 0.1 mM to about 15 mM, even more typically from about 1 mM to about 11 mM, with working embodiments typically comprising from about 5 to about 5.5 mM DAB chromogen, and/or derivatives thereof.

B. Polymers

Various polymers can be used in the disclosed composition. A suitable polymer contemplated by the present disclosure typically is a water-soluble polymer comprising a polymeric backbone and at least one, and typically plural functional groups that are effective to reduce or substantially preclude precipitation of the DAB chromogen, and/or derivatives thereof. Reactive chemical initiators used in connection with polymer synthesis will often leave functional groups on the terminal positions of polymeric chains. While these groups can affect the solubility and functionality of the polymer, especially for low molecular weight polymers, the functionality described herein relates to the functional groups spanning the polymer backbones. In illustrative embodiments, polymers having been initiated with reactive initiators with functional groups providing additional operability within the scope of the current disclosure are included in the disclosed composition.

1. Polymeric Backbones

Certain embodiments of disclosed polymers include a polymeric backbone. The polymeric backbone may be water soluble or substantially water insoluble. In embodiments wherein the polymeric backbone itself is substantially water insoluble, the entire polymer (e.g. polymeric backbone in combination with suitable functional groups) should be substantially water soluble. Particular disclosed embodiments concern polymeric backbones having either one of Formulas 1, 2, and 3, illustrated below.

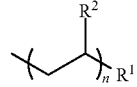

Formula 1

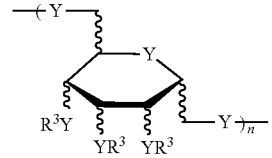

Formula 2

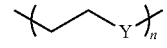

Formula 3

With reference to Formula 1, $R^1$ may be selected from aliphatic, aryl, heteroaryl, and a heteroatom-containing moiety. In one embodiment, $R^1$ may further comprise any of the suitable polymeric functional groups disclosed herein. The heteroatom containing moiety may be selected from ester, acid, and amide. $R^2$ may be selected from hydrogen, aliphatic, heteroaliphatic, aryl, or heteroaryl. With reference to Formulas 3 and 2, each Y independently may be selected from oxygen, sulfur, and $NR^a$ wherein $R^a$ is selected from hydrogen, aliphatic, aryl, heteroaryl, and heteroaliphatic. $R^3$ may be selected from any of the suitable polymeric functional groups disclosed herein, and n ranges from 1 to about 100.

In one embodiment, the polymer may have a Formula 4 or 5, illustrated below.

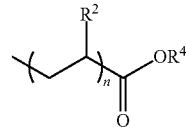

Formula 4

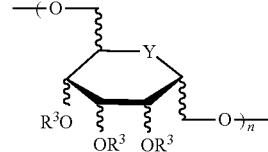

Formula 5

With reference to Formulas 4 and 5, $R^2$ may be selected from hydrogen, aliphatic, heteroaliphatic, aryl, or heteroaryl and $R^3$ may be a polymer functional group selected from a sulfonate, an amine, a carboxyl group, a carboxylate, or combinations thereof. $R^4$ may be selected from hydrogen, aliphatic, and $(CH_2)_q NR^a R^b R^c$ wherein $R^a$, $R^b$, and $R^c$ independently are selected from hydrogen, aliphatic, aryl, and combinations thereof, and q ranges from 1 to about 10; and n ranges from 1 to about 100.

Furthermore, any one of the disclosed polymeric backbones may be combined with another polymeric backbone in order to produce a hybrid polymeric backbone.

Particular disclosed embodiments concern polymeric backbones selected from dextrans, polystyrene, polyvinyl derivatives, polymethacrylate derivatives, polyacrylamide derivatives, polysaccharide derivatives, polypeptide derivatives, nucleic acid and nucleic acid backbone derivatives, polystyrene/maleic acid co-polymers, poly(acrylamide/methacrylate) co-polymers, and the like.

Examples of suitable water-soluble moieties include dextran polymers. Dextrans are readily soluble in water, salt, and electrolyte containing compositions, and pH has a negligible effect on solubility. Concentrated dextran solutions, such as solutions comprising greater than 50% (w/v) can be prepared. A person of ordinary skill in the art will recognize that dextrans have various molecular weights.

Other polymeric backbones can be based on less soluble, or substantially non-soluble backbones, as long as the polymeric material used to form disclosed compositions is itself substantially water soluble. Examples of this class of backbones include aryl backbones, such as exemplified by styrene-type polymeric materials.

2. Suitable Polymeric Functional Groups

Suitable functional groups include any functional groups that facilitate maintaining a DAB chromogen, and/or derivatives thereof, in solution during and after product formulation. By way of example, suitable functional groups include carboxylate, sulfonate (R—SO$_2$O$^-$), sulfate (SO$_4^{2-}$), amine, including primary, secondary, tertiary and quaternary amines, substituted amines, and combinations of such functional groups. An amine functional group may be selected from aliphatic amines, particularly amines functionalized with one or more hydrogen atoms or one or more lower alkyl groups, such as methyl, ethyl, propyl, and butyl groups; aryl amines, such as amines functionalized with one or more aryl groups, particularly phenyl; heteroaryl amines; and combinations thereof. In one embodiment, the polymer may be a polyalkyleneamine.

3. Exemplary Polymers

Figure 3:
FIG. 3 is an image of a tonsil tissue section stained for Ki67 with a DAB chromogen solution.
Figure 4:
FIG. 4 is an image of a tonsil tissue section stained for Ki67 with a DAB chromogen solution and polystyrene sulfonate (PSS) polymer having a Mw=1.5 kDa (5 wt %).
Figure 5:
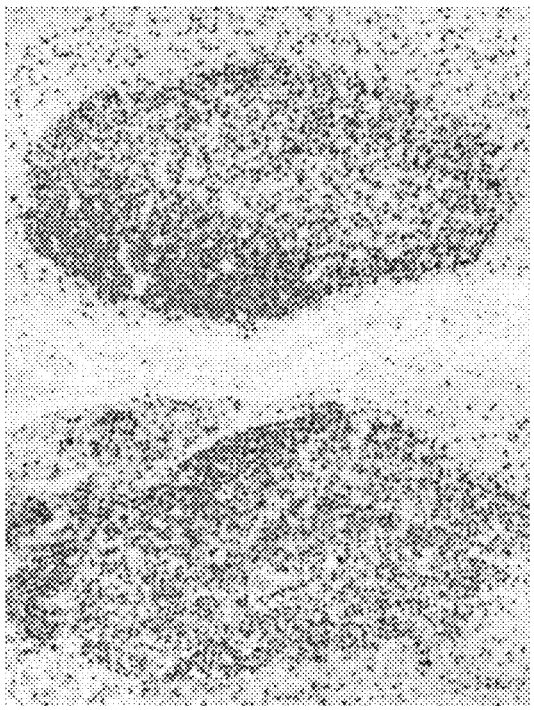
FIG. 5 is an image of a tonsil tissue section stained with for Ki67 a DAB chromogen solution and PSS polymer having a Mw=5.1 kDa (5 wt %).
Figure 6:
FIG. 6 is an image of a tonsil tissue section stained for Ki67 with a DAB chromogen solution and PSS polymer having a Mw=7.5 kDa (5 wt %).
Figure 7:
FIG. 7 is an image of a tonsil tissue section stained for Ki67 with a DAB chromogen solution and PSS polymer having a Mw=16 kDa (5 wt %).
Figure 8:
FIG. 8 is an image of a tonsil tissue section stained for Ki67 with a DAB chromogen solution and PSS polymer having a Mw=35 kDa (5 wt %).

The following polymers are meant only to be exemplary of classes and species of polymers suitable for forming the disclosed composition and are not intended to be limiting. Sulfonate and sulfate polymers substantially reduce or prevent DAB sulfate precipitation apparently by forming a water-soluble polymer complex with DAB, and/or derivatives thereof. The effect of the sulfate and sulfonate polymers on DAB chromogen tissue staining also may be controlled by varying the polymer size, such as weight average molecular weight (Mw) and/or number average molecular weight (Mn) and/or the polymer wt % concentration. DAB chromogen tissue staining was reduced and hematoxylin background staining increased with larger Mw polymers. For example, FIGS. 3-8 collectively illustrate the effects of exemplary working embodiments on DAB deposition with increasing polystyrene sulfonate (PSS) polymer Mw. FIG. 3 is a control image of a stained tissue section produced using a composition comprising solely a DAB chromogen solution (e.g. an OPTIVIEW® DAB solution, Ventana Medical Systems, Inc. Tucson AZ, hereinafter referred to as "Ventana"). FIGS. 4-8 are images of stained tissue sections produced using a composition comprising a DAB chromogen solution and PSS polymer having molecular weights of about 1.5 kDa (FIG. 4), 5.1 kDa (FIG. 5), 7.5 kDa (FIG. 6), 16 kDa (FIG. 7), and 35 kDa (FIG. 8). All polymers used in these exemplary embodiments were used at a polymer concentration of 5 wt %. As illustrated in FIGS. 4-8, higher molecular weight derivatives of PSS polymers lead to decreased DAB staining and increased hematoxylin background staining. In exemplary embodiments, low molecular weight dextran sulfate and polystyrene sulfate address DAB sulfate precipitation with a minimal impact on DAB tissue staining.

Amine polymers also are useful for reducing, or substantially preventing, DAB sulfate precipitation. In one embodiment, amine polymers may be used to completely inhibit precipitation of DAB, and/or derivatives thereof. Primary, secondary, tertiary and quaternary amine polymers are contemplated by the present disclosure. Amine polymers do not have the same impact on DAB tissue staining as sulfate and sulfonate polymers. Without being bound to a particular theory of operation, it is currently believed that polymer concentration can increase viscosity and therefore can affect DAB tissue staining. Amine polymers may substantially reduce or prevent DAB sulfate precipitation by forming a water-soluble polymer complex between the cationic polymer and sulfate anions, thereby reducing the concentration of free sulfate available for complexing with DAB and forming the insoluble DAB sulfate complex. Tissue staining can also be affected by amine polymer solubility, which can be an issue at neutral pH in reaction buffer for particular embodiments of amine polymers, such as Mw=15 kDa polyallylamine. Suitable exemplary polymers of amines include, but are not limited to, polyethyleneimine (linear or branched), dextran DEAE and poly(2-methylacryloxethyltrimethyl-ammonium bromide) polymers.

Figure 9:
FIG. 9 is an image of a control slide wherein the tonsil tissue sample is stained for Ki67 with a DAB chromogen solution.
Figure 10:
FIG. 10 is an image of a tonsil tissue section stained for Ki67 with a DAB chromogen solution and aminodextran polymer having a Mw=10 kDa.
Figure 11:
FIG. 11 is an image of a tonsil tissue section stained for Ki67 with a DAB chromogen solution and aminodextran polymer having a Mw=40 kDa.
Figure 12:
FIG. 12 is an image of a tonsil tissue section stained for Ki67 with a DAB chromogen solution and aminodextran polymer having a Mw=70 kDa.

In one embodiment, the composition comprises a chromogen, or chromogens, and an aminodextran polymer. FIGS. 9-12 collectively illustrate the results of certain working embodiments using the disclosed composition. FIG. 9 is an image illustrating results obtained with a control wherein only the DAB chromogen solution was applied to a tissue sample. FIGS. 10-12 are images of stained tissue sections wherein a composition comprising the DAB chromogen solution and 4 wt % of aminodextran having varying molecular weights was added to the tissue section. FIG. 10 illustrates results obtained with a Mw=10 kDa aminodextran polymer, FIG. 11 concerns a Mw=40 kDa aminodextran polymer, and FIG. 12 illustrates results obtained using a Mw=70 kDa aminodextran polymer. Polymer concentration (wt %) of the aminodextran-based polymers typically has less impact on tissue staining; however, optimization of the polymer concentration may be carried out in order to promote polymer solubility and DAB sulfate precipitate prevention.

In other disclosed embodiments, DAB chromogen solutions containing varying polymer concentrations, such as 0.05 to 3 wt %, of linear polyethyleneimine (PEI, 2.5 kDa free base or corresponding 4 kDa HCl salt) can be used to address DAB sulfate precipitation. This disclosed embodiment may be used with DAB chromogen solutions comprising up to about 4 mM of an antioxidant stabilizer, such as sodium metabisulfite and typically will not negatively impact DAB tissue staining. Other classes of amine polymers, such as dextran DEAE and aminodextran, were found to significantly reduce DAB sulfate precipitation with up to about 1 mM of an antioxidant stabilizer, such as sodium metabisulfite, without negatively impacting DAB tissue staining; however, these particular disclosed embodiments typically provide minimum protection against DAB sulfate precipitation at about 4 mM sodium metabisulfite. Other disclosed embodiments of amine polymers include branched PEI and polyallylamine, which may be used to prevent precipitation at stabilizer levels of about 1 mM to about 4 mM. However, in one embodiment, these amine polymers may not produce desired DAB staining of the tissue sample.

Based on the above, an exemplary list of particular species of polymeric materials suitable for the present invention includes dextran sulfate, polystyrene sulfonate, polystyrene sulfonate maleic acid co-polymer, linear polyethyleneimine, dextran DEAE, aminodextran, poly(2-vinyl-1-methylpyridinium bromide), poly(2-methylacryloxethyltrimethylammonium bromide), poly(acrylamide/2-methylacryloxethyltrimethylammonium bromide), and combinations thereof.

C. DAB/Polymer Ratio, Molecular Weights, and Concentrations

In one embodiment, low molecular weight polymers tend to have less of an impact on DAB staining. The ability to influence counterstaining (e.g. hematoxylin counterstaining) may also be controlled by manipulating polymer wt % and molecular weight. Particular disclosed embodiments concern a composition comprising a DAB chromogen solution comprising DAB chromogen, and/or derivatives thereof, in a concentration ranging from greater than 0.1 mM to about 100 mM, more typically from greater than 0.5 mM to about 15 mM, even more typically from about 1 mM to about 11 mM, with working embodiments typically comprising from about 5 to about 11 mM of DAB, and/or derivatives thereof. Disclosed embodiments of the composition also comprise one or more of the disclosed polymers or equivalents thereof wherein the polymer has a molecular weight ranging from greater than 1 kDa to about 500 kDa, more typically from about 1 kDa to about 250 kDa, even more typically from about 1 kDa to about 100 kDa. The polymer has a polymer concentration ranging from greater than 0.01 to about 10 weight percent, more typically from about 0.1 to about 7 weight percent.

In disclosed embodiments where the polymer is a dextran sulfate polymer, the molecular weight of the polymer will typically range from about 5 kDa to about 30 kDa at a polymer concentration of from about 2 to about 5 weight percent. Even more typically, the dextran sulfate polymer has a molecular weight ranging from about 6.5 kDa to about 20 kDa at a polymer concentration of from about 2 to about 5 weight percent. If the polymer is a polystyrene sulfonate polymer, then typical embodiments will have a molecular weight ranging from about 1 kDa to about 40 kDa at a polymer concentration of from about 2 to about 5 weight percent. Even more typically, the polystyrene sulfonate polymer will have a molecular weight ranging from about 1 kDa to about 35 kDa at a polymer concentration of from about 2 to about 5 weight percent. Exemplary working embodiments used a polystyrene sulfonate polymer having a molecular weight of about 1.5 kDa and a polymer concentration of 2 weight percent. If the composition comprises a polystyrene sulfonate maleic acid co-polymer, then the polymer typically will have a molecular weight of greater than 0 kDa to about 20 kDa and a polymer concentration of greater than 2 to about 5 weight percent. If the composition comprises a polyvinvylsulfonate polymer, then the polymer typically will have a molecular weight of from about 4 to about 6 kDa and a polymer concentration of greater than 2 to about 5 weight percent.

If the composition comprises an aminodextran polymer, then the polymer typically will have a molecular weight ranging from about 10 kDa to about 70 kDa at a polymer concentration of from greater than 0.1 to about 10 weight percent, more typically from about 0.25 to about 5 weight percent. If the composition comprises a dextran DEAE polymer, then the polymer typically will have a molecular weight ranging from greater than 1 kDa to about 500 kDa and a polymer concentration ranging from greater than 0.1 to about 7 weight percent. In other disclosed embodiments, the composition may comprise a polyallylamine polymer having a molecular weight of greater than 1 kDa to about 15 kDa and a polymer concentration ranging from greater than 0.01 to about 5 weight percent. In exemplary embodiments, the composition comprises a polyethyleneimine polymer having a molecular weight of about 2.5 kDa and a polymer concentration of about 0.15 weight percent. The polyethyleneimine polymer may be selected from a free base polymer or a salt, wherein the salt typically is a 4 kDa HCl salt of the same corresponding 2.5 kDa polyethyleneimine free base polymer.

D. DAB Base Formulations

One embodiment of a DAB base solution comprises DAB chromogen, one or more enhancers, and a stabilizer. In one embodiment, the DAB base solution comprises a DAB chromogen, and/or derivatives thereof, having a concentration ranging from greater than 0.1 mM to about 15 mM, more typically from greater than 0.1 mM to about 11 mM, an imidazole enhancer having a concentration ranging from greater than 0.01 mM to about 15 mM, a 2-hydroxypyridine enhancer having a concentration ranging from greater than 0.01 mM to about 15 mM, and a sodium metabisulfite stabilizer having a concentration ranging from greater than 0.01 mM to about 2 mM. Exemplary base solutions comprise 5.5 mM DAB, 10 mM imidazole, 10 mM 2-hydroxypyridine, and 1 mM sodium metabisulfite, with a pH of 2.5±0.1. In one embodiment, these compositions were tested using $KHSO_4$ concentrations ranging from 0 to about 10 mM; more typically 0, 1.37, 2.75 and 8.0 mM, with DAB sulfate precipitation being induced at 4° C. overnight. In another embodiment, the enhancer is omitted from the DAB base formulation and included in the oxidant formulation, as disclosed herein, in concentrations equivalent to those specified herein.

Certain DAB chromogen compositions are known, and are commercially available, which do not include a polymeric stabilizer as is used with embodiments disclosed in the present application. For example, Ventana Medical Systems, Inc., provides a DAB chromogen formulation comprising 5.5 mM DAB·4HCl, 10 mM imidazole, 10 mM 2-hydroxypyridine, 1 mM sodium metabisulfite, 5 wt % PEG8000, 0.05% w/v Brij 35, and 750 µM sodium stannate trihydrate, with a pH of 2.3±0.1.

A person of ordinary skill in the art will recognize that sodium metabisulfite disproportionates in water to form 2 moles of sodium bisulfite per mole of sodium metabisultite. Each mole of sodium bisulfite can form one mole of sodium hydrogen sulfate which can form an insoluble salt complex with DAB. In one embodiment, DAB sulfate was determined to most likely be a DAB monosulfate salt by analysis.

Certain disclosed embodiments of a new DAB chromogen composition developed by Ventana Medical Systems, Inc. comprise 5.5 mM DAB·4HCl, 10 mM imidazole, 10 mM 2-hydroxypyridine, 1 mM sodium metabisulfite, 0.15 wt % 2.5 kDa linear PEI (free base or 4 kDa HCl salt polymers), and 0.05% w/v Brij 35, with a pH of 2.3±0.1. Other embodiments of DAB chromogen compositions comprise 0.15 wt % 2.5 kDa linear PEI (free base or 4 kDa HCl salt), 5-7 wt % 500 kDa dextran DEAE, 2 wt % 6.5-10 kDa dextran sulfate and 2 wt %~1.5 kDa PSS polymers.

IV. Method of Using the Composition

The present disclosure also concerns embodiments of a method for using DAB chromogen compositions disclosed herein. In one embodiment, the method may comprise providing a tissue sample comprising an epitope; exposing the tissue sample to a labeled specific binding moiety and a labeled enzyme; exposing the tissue sample to a composition comprising DAB chromogen, or derivative thereof, in an amount effective for a tissue staining procedure, an effective amount of stabilizer, and polymer in an amount effective to reduce or substantially prevent DAB precipitation relative to a composition that does not include the polymer; exposing the tissue sample to an oxidant and a counterstain; and detecting the epitope.

In one embodiment, the tissue sample may be any tissue sample capable of being analyzed using colorimetric detection. Particular disclosed embodiments concern using a formalin-fixed, paraffin-embedded tissue sample. The labeled specific binding moiety may be labeled with a first member of a specific binding pair, such as a hapten (e.g. an oxazole, a pyrazole, a thiazole, a nitroaryl compound other than dinitrophenyl, a benzofurazan, a triterpene, a urea, a thiourea, a rotenoid, a coumarin, a cyclolignan, a heterobiaryl, an azo aryl, or a benzodiazepine). In one embodiment, the hapten is selected from HQ, DIG, DNP, TS, NP, DCC, and biotin. Exemplary haptens and conjugates comprising haptens are disclosed in U.S. Pat. No. 7,695,929, which is incorporated herein by reference. The specific binding moiety may be selected from an antibody or a nucleic acid (e.g. DNA or RNA). In one embodiment, the labeled enzyme is an enzyme that is conjugated with a second member of a specific binding pair, such as an antibody or avidin (e.g. streptavidin). The enzyme may be a peroxidase, such as horseradish peroxidase.

The tissue sample may be exposed to the disclosed composition using a variety of different techniques. In one embodiment, the tissue sample is exposed to the composition by adding separate solutions of the DAB chromogen and the polymer to the tissue sample simultaneously, by sequentially adding separate solutions of the DAB chromogen and the polymer to the tissue sample, or by adding a solution comprising DAB chromogen and the polymer to the tissue sample. The composition may comprise any of the disclosed components described herein. After addition of the disclosed composition, an oxidant, such as hydrogen peroxide, may be added to the tissue sample. Also, a counterstain, such as hematoxylin may be added to the tissue sample. An epitope within the tissue sample may then be detected using colorimetric detection. The disclosed method may be performed manually or may be partially or fully automated.

V. Kits

The present disclosure also contemplates embodiments of a kit comprising the disclosed composition. In one embodiment, the disclosed kit may comprise DAB chromogen, or derivative thereof; an enhancer selected from imidazole, 2-hydroxypyridine, and combinations thereof; an antioxidant stabilizer, such as sodium metabisulfite; and polymer capable of reducing or preventing DAB sulfate precipitation relative to a composition that does not include the polymer. The reagents may be packaged separately, or two or more reagents may be in the same solution.

VI. Samples and Targets

The disclosed composition may be used to detect one or more targets in a sample. Samples include biological components and generally are suspected of including one or more target molecules of interest. Target molecules can be on the surface of cells and the cells can be in a suspension, or in a tissue section. Target molecules can also be intracellular and detected upon cell lysis or penetration of the cell by a probe. One of ordinary skill in the art will appreciate that the method of detecting target molecules in a sample will vary depending upon the type of sample and probe being used. Methods of collecting and preparing samples are known in the art.

Samples for use in the embodiments of the method and with the composition disclosed herein, such as a tissue or other biological sample, can be prepared using any method known in the art by of one of ordinary skill. The samples can be obtained from a subject for routine screening or from a subject that is suspected of having a disorder, such as a genetic abnormality, infection, or a neoplasia. The described embodiments of the disclosed method can also be applied to samples that do not have genetic abnormalities, diseases, disorders, etc., referred to as "normal" samples. Such normal samples are useful, among other things, as controls for comparison to other samples. The samples can be analyzed for many different purposes. For example, the samples can be used in a scientific study or for the diagnosis of a suspected malady, or as prognostic indicators for treatment success, survival, etc.

Samples can include multiple targets that can be specifically bound by a probe or reporter molecule. The targets can be nucleic acid sequences or proteins. Throughout this disclosure when reference is made to a target protein it is understood that the nucleic acid sequences associated with that protein can also be used as a target. In some examples, the target is a protein or nucleic acid molecule from a pathogen, such as a virus, bacteria, or intracellular parasite, such as from a viral genome. For example, a target protein may be produced from a target nucleic acid sequence associated with (e.g., correlated with, causally implicated in, etc.) a disease.

A target nucleic acid sequence can vary substantially in size. Without limitation, the nucleic acid sequence can have a variable number of nucleic acid residues. For example a target nucleic acid sequence can have about 10 nucleic acid residues, or about 20, 30, 50, 100, 150, 500, 1000 residues. Similarly, a target polypeptide can vary substantially in size. Without limitation, the target polypeptide will include epitope that binds to a peptide specific antibody, or fragment thereof. In some embodiments that polypeptide can include two epitopes that bind to a peptide specific antibody, or fragment thereof.

In specific, non-limiting examples, a target protein is produced by a target nucleic acid sequence (e.g., genomic target nucleic acid sequence) associated with a neoplasm (for example, a cancer). Numerous chromosome abnormalities (including translocations and other rearrangements, amplification or deletion) have been identified in neoplastic cells, especially in cancer cells, such as B cell and T cell leukemias, lymphomas, breast cancer, colon cancer, neurological cancers and the like. Therefore, in some examples, a portion of the target molecule is produced by a nucleic acid sequence (e.g., genomic target nucleic acid sequence) amplified or deleted in a subset of cells in a sample.

Oncogenes are known to be responsible for several human malignancies. For example, chromosomal rearrangements involving the SYT gene located in the breakpoint region of chromosome 18q11.2 are common among synovial sarcoma soft tissue tumors. The t(18q11.2) translocation can be identified, for example, using probes with different labels: the first probe includes FPC nucleic acid molecules generated from a target nucleic acid sequence that extends distally from the SYT gene, and the second probe includes FPC nucleic acid generated from a target nucleic acid sequence that extends 3' or proximal to the SYT gene. When probes corresponding to these target nucleic acid sequences (e.g., genomic target nucleic acid sequences) are used in an in situ hybridization procedure, normal cells, which lack a t(18q11.2) in the SYT gene region, exhibit two fusion (generated by the two labels in close proximity) signals, reflecting the two intact copies of SYT. Abnormal cells with a t(18q11.2) exhibit a single fusion signal.

In other examples, a target protein produced from a nucleic acid sequence (e.g., genomic target nucleic acid sequence) is selected that is a tumor suppressor gene that is deleted (lost) in malignant cells. For example, the p16 region (including D9S1749, D9S1747, p16(INK4A), p14(ARF), D9S1748, p15(INK4B), and D9S1752) located on chromosome 9p21 is deleted in certain bladder cancers. Chromosomal deletions involving the distal region of the short arm of chromosome 1 (that encompasses, for example, SHGC57243, TP73, EGFL3, ABL2, ANGPTL1, and SHGC-1322), and the pericentromeric region (e.g., 19p13-19q13) of chromosome 19 (that encompasses, for example, MAN2B1, ZNF443, ZNF44, CRX, GLTSCR2, and GLTSCR1) are characteristic molecular features of certain types of solid tumors of the central nervous system.

The aforementioned examples are provided solely for purpose of illustration and are not intended to be limiting. Numerous other cytogenetic abnormalities that correlate with neoplastic transformation and/or growth are known to those of ordinary skill in the art. Target proteins that are produced by nucleic acid sequences (e.g., genomic target nucleic acid sequences), which have been correlated with neoplastic transformation and which are useful in the disclosed methods, also include the EGFR gene (7p12; e.g., GENBANK™ Accession No. NC_000007, nucleotides 55054219-55242525), the C-MYC gene (8q24.21; e.g., GENBANK™ Accession No. NC_000008, nucleotides 128817498-128822856), D5S271 (5p15.2), lipoprotein lipase (LPL) gene (8p22; e.g., GENBANK™ Accession No. NC_000008, nucleotides 19841058-19869049), RB1 (13q14; e.g., GENBANK™ Accession No. NC_000013, nucleotides 47775912-47954023), p53 (17p13.1; e.g., GENBANK™ Accession No. NC_000017, complement, nucleotides 7512464-7531642)), N-MYC (2p24; e.g., GENBANK™ Accession No. NC_000002, complement, nucleotides 151835231-151854620), CHOP (12q13; e.g., GENBANK™ Accession No. NC_000012, complement, nucleotides 56196638-56200567), FUS (16p11.2; e.g., GENBANK™ Accession No. NC_000016, nucleotides 31098954-31110601), FKHR (13p14; e.g., GENBANK™ Accession No. NC_000013, complement, nucleotides 40027817-40138734), as well as, for example: ALK (2p23; e.g., GENBANK™ Accession No. NC_000002, complement, nucleotides 29269144-29997936), Ig heavy chain, CCND1 (11q13; e.g., GENBANK™ Accession No. NC_000011, nucleotides 69165054 . . . 69178423), BCL2 (18q21.3; e.g., GENBANK™ Accession No. NC_000018, complement, nucleotides 58941559-59137593), BCL6 (3q27; e.g., GENBANK™ Accession No. NC_000003, complement, nucleotides 188921859-188946169), MALF1, AP1 (1p32-p31; e.g., GENBANK™ Accession No. NC_000001, complement, nucleotides 59019051-59022373), TOP2A (17q21-q22; e.g., GENBANK™ Accession No. NC_000017, complement, nucleotides 35798321-35827695), TMPRSS (21q22.3; e.g., GENBANK™ Accession No. NC_000021, complement, nucleotides 41758351-41801948), ERG (21q22.3; e.g., GENBANK™ Accession No. NC_000021, complement, nucleotides 38675671-38955488); ETV1 (7p21.3; e.g., GENBANK™ Accession No. NC_000007, complement, nucleotides 13897379-13995289), EWS (22q12.2; e.g., GENBANK™ Accession No. NC_000022, nucleotides 27994271-28026505); FLIT (11q24.1-q24.3; e.g., GENBANK™ Accession No. NC_000011, nucleotides 128069199-128187521), PAX3 (2q35-q37; e.g., GENBANK™ Accession No. NC_000002, complement, nucleotides 222772851-222871944), PAX7 (1p36.2-p36.12; e.g., GENBANK™ Accession No. NC_000001, nucleotides 18830087-18935219), PTEN (10q23.3; e.g., GENBANK™ Accession No. NC_000010, nucleotides 89613175-89716382), AKT2 (19q13.1-q13.2; e.g., GENBANK™ Accession No. NC_000019, complement, nucleotides 45431556-45483036), MYCL1 (1p34.2; e.g., GENBANK™ Accession No. NC_000001, complement, nucleotides 40133685-40140274), REL (2p13-p12; e.g., GENBANK™ Accession No. NC_000002, nucleotides 60962256-61003682) and CSF1R (5q33-q35; e.g., GENBANK™ Accession No. NC_000005, complement, nucleotides 149413051-149473128).

In other examples, a target protein is selected from a virus or other microorganism associated with a disease or condition. Detection of the virus- or microorganism-derived target nucleic acid sequence (e.g., genomic target nucleic acid sequence) in a cell or tissue sample is indicative of the presence of the organism. For example, the target peptide, polypeptide or protein can be selected from the genome of an oncogenic or pathogenic virus, a bacterium or an intracellular parasite (such as *Plasmodium falciparum* and other *Plasmodium* species, *Leishmania* (sp.), *Cryptosporidium parvum, Entamoeba histolytica*, and *Giardia lamblia*, as well as *Toxoplasma, Eimeria, Theileria*, and *Babesia* species).

In some examples, the target protein is produced from a nucleic acid sequence (e.g., genomic target nucleic acid sequence) from a viral genome. Exemplary viruses and corresponding genomic sequences (GENBANK™ RefSeq Accession No. in parentheses) include human adenovirus A (NC_001460), human adenovirus B (NC_004001), human adenovirus C (NC_001405), human adenovirus D (NC_002067), human adenovirus E (NC_003266), human adenovirus F (NC_001454), human astrovirus (NC_001943), human BK polyomavirus (V01109; GI:60851) human bocavirus (NC_007455), human coronavirus 229E (NC_002645), human coronavirus HKU1 (NC_006577), human coronavirus NL63 (NC_005831), human coronavirus OC43 (NC_005147), human enterovirus A (NC_001612), human enterovirus B (NC_001472), human enterovirus C (NC_001428), human enterovirus D (NC_001430), human erythrovirus V9 (NC_004295), human foamy virus (NC_001736), human herpesvirus 1 (Herpes simplex virus type 1) (NC_001806), human herpesvirus 2 (Herpes simplex virus type 2) (NC_001798), human herpesvirus 3 (Varicella zoster virus) (NC_001348), human herpesvirus 4 type 1 (Epstein-Barr virus type 1) (NC_007605), human herpesvirus 4 type 2 (Epstein-Barr virus type 2) (NC_009334), human herpesvirus 5 strain AD169 (NC_001347), human herpesvirus 5 strain Merlin Strain (NC_006273), human herpesvirus 6A (NC_001664), human herpesvirus 6B (NC_000898), human herpesvirus 7 (NC_001716), human herpesvirus 8 type M (NC_003409), human herpesvirus 8 type P (NC_009333), human immunodeficiency virus 1 (NC_001802), human immunodeficiency virus 2 (NC_001722), human metapneumovirus (NC_004148), human papillomavirus-1 (NC_001356), human papillomavirus-18 (NC_001357), human papillomavirus-2 (NC_001352), human papillomavirus-54 (NC_001676), human papillomavirus-61 (NC_001694), human papillomavirus-cand90 (NC_004104), human papillomavirus RTRX7 (NC_004761), human papillomavirus type 10 (NC_001576), human papillomavirus type 101 (NC_008189), human papillomavirus type 103 (NC_008188), human papillomavirus type 107 (NC_009239), human papillomavirus type 16 (NC_001526), human papillomavirus type 24 (NC_001683), human papillomavirus type 26 (NC_001583), human papillomavirus type 32 (NC_001586), human papillomavirus type 34 (NC_001587), human papillomavirus type 4 (NC_001457), human papillomavirus type 41 (NC_001354), human papillomavirus type 48 (NC_001690), human papillomavirus type 49 (NC_001591), human papillomavirus type 5 (NC_001531), human papillomavirus type 50 (NC_001691), human papillomavirus type 53 (NC_001593), human papillomavirus type 60 (NC_001693), human papillomavirus type 63 (NC_001458), human papillomavirus type 6b (NC_001355), human papillomavirus type 7 (NC_001595), human papillomavirus type 71 (NC_002644), human papillomavirus type 9 (NC_001596), human papillomavirus type 92 (NC_004500), human papillomavirus type 96 (NC_005134), human parainfluenza virus 1 (NC_003461), human parainfluenza virus 2 (NC_003443), human parainfluenza virus 3 (NC_001796), human parechovirus (NC_001897), human parvovirus 4 (NC_007018), human parvovirus B19 (NC_000883), human respiratory syncytial virus (NC_001781), human rhinovirus A (NC_001617), human rhinovirus B (NC_001490), human spumaretrovirus (NC_001795), human T-lymphotropic virus 1 (NC_001436), human T-lymphotropic virus 2 (NC_001488).

In certain examples, the target protein is produced from a nucleic acid sequence (e.g., genomic target nucleic acid sequence) from an oncogenic virus, such as Epstein-Barr Virus (EBV) or a Human Papilloma Virus (HPV, e.g., HPV16, HPV18). In other examples, the target protein produced from a nucleic acid sequence (e.g., genomic target nucleic acid sequence) is from a pathogenic virus, such as a Respiratory Syncytial Virus, a Hepatitis Virus (e.g., Hepatitis C Virus), a Coronavirus (e.g., SARS virus), an Adenovirus, a Polyomavirus, a Cytomegalovirus (CMV), or a Herpes Simplex Virus (HSV).

VII. Working Embodiments

The following examples are provided to exemplify certain details of working embodiments. A person of ordinary skill in the art will appreciate that the present invention is not limited to those specific features exemplified by these examples.

A. General Procedures

1. Polymer Screening

Polymers were screened for their impact on DAB sulfate precipitation formation by combining an enhanced DAB base solution containing a set amount of the polymer with select molar ratios of potassium hydrogen sulfate, $KHSO_4$, relative to DAB. The enhanced DAB base solution used comprised 5.5 mM DAB·4HCl, 10 mM imidazole, 10 mM 2-hydroxypyridine, 1 mM sodium metabisulfite and 0.05% w/v Brij 35 at pH=2.3±0.1. The potassium hydrogen sulfate concentrations screened were 2.75 and 8.0 mM. The solutions were mixed vigorously at room temperature for 15 seconds and then stored at 2-8° C. to induce DAB sulfate precipitation. Solutions were monitored for physical changes (i.e. color or precipitation). The candidate solutions were analyzed by HPLC before and after sulfate addition to confirm changes in DAB concentration relative to 2-hydroxypyridine as an internal standard.

2. Immunohistochemistry Staining Procedure

All immunohistochemistry was performed on a Ventana Benchmark XT automated staining platform using components of either the VENTANA OPTIVIEW® DAB (Ventana Medical Systems, Inc. Catalog #760-700) or iView DAB (Ventana Medical Systems, Inc. Catalog #760-091) detection kits following suggested product insert protocols. Antigen detection was performed using either CONFIRM® anti-Ki67 (30-9) antibody (Ventana #790-4286) or anti-CD10 (SP67) antibody (Ventana #790-4056) by adding one drop of either antibody and incubating at 37° C. for 16 minutes. DAB IHC Detection was achieved by adding one drop of the candidate DAB chromogen solution, followed by one drop of the appropriate $H_2O_2$ solution and co-incubating for 8 minutes. Slides were counterstained with Hematoxylin II (Ventana #790-2208) for 4 minutes, followed by Bluing (Ventana 760-2037) for four minutes. The slides were rinsed with a detergent water mixture, dehydrated through gradient alcohol and xylene baths and coverslipped.

3. HPLC Analytical Method

Figure 13:
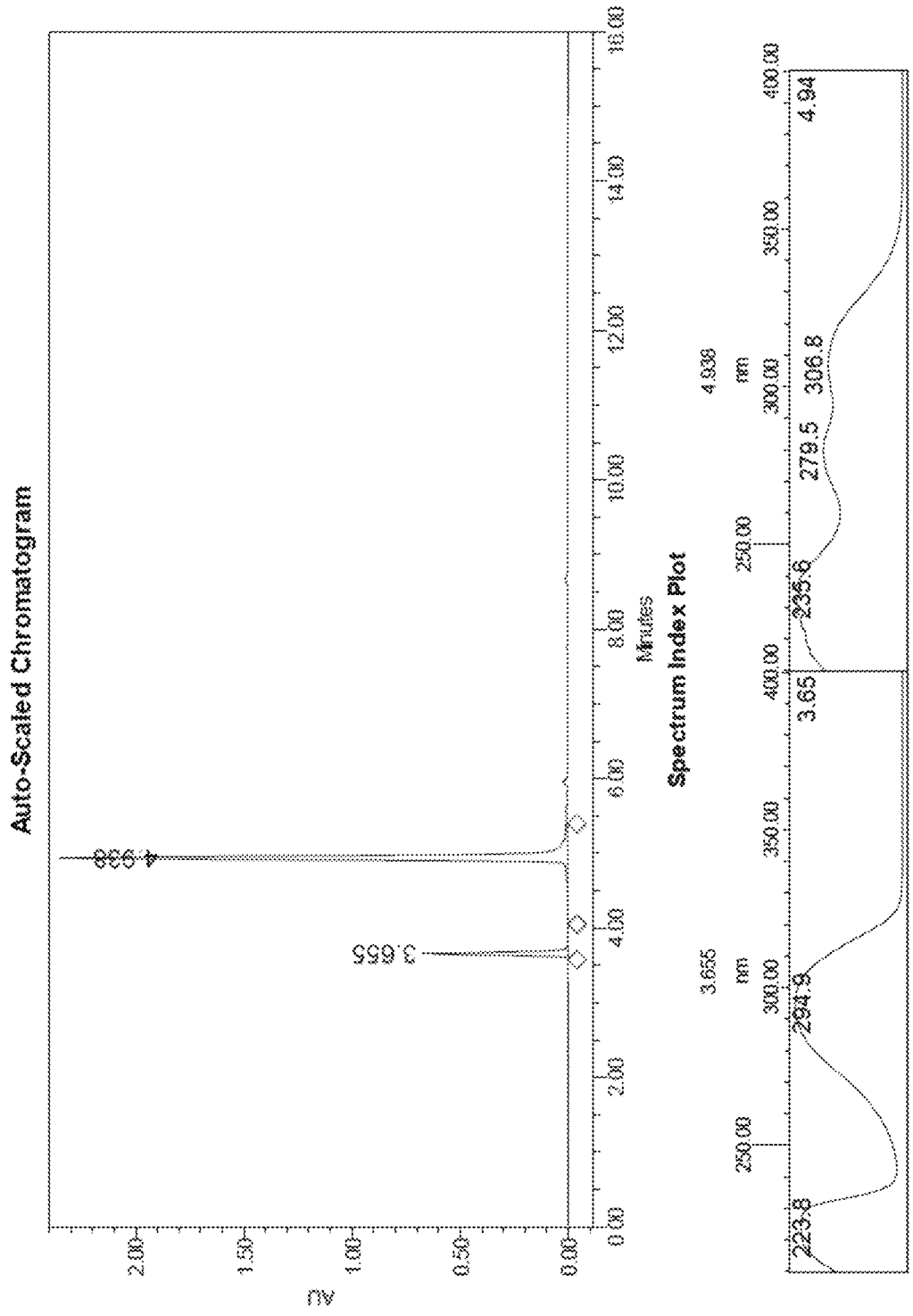
FIG. 13 is an image of a representative HPLC trace and a spectrum index plot.

HPLC analysis was performed using the method below and FIG. 13 illustrates representative HPLC spectra obtained using this exemplary method.

Column: Waters Xbridge RP-C18 Column 4.6×150 mm (5 µ) [Phenomenex C18 Security guard column]

Eluents: A: deionized water, C: acetonitrile, D: 100 mM aq. ammonium acetate (pH=5.0)

Flow rate: 1 mL/min

Gradient profile:

| Time (min) | % A | % C | % D |
|---|---|---|---|
| 0 | 83 | 1 | 16 |
| 10 | 4 | 80 | 16 |
| 12 | 4 | 80 | 16 |
| 13 | 83 | 1 | 16 |
| 16 | 83 | 1 | 16 |

Injection volume: 3 µL of DAB chromogen solution without dilution
Detection wavelength: 260 nm
Retention time: DAB (4.94 min), 2-hydroxypyridine (3.65 min)

EXAMPLES

Example 1

Candidate polymers were screened for their impact on DAB sulfate precipitation formation by combining an enhanced DAB base solution containing a set amount of the polymer with select molar ratios of potassium hydrogen sulfate, $KHSO_4$, relative to DAB. The enhanced DAB base solution used comprised 5.5 mM DAB·4HCl, 10 mM imidazole, 10 mM 2-hydroxypyridine, 1 mM sodium metabisulfite and 0.05% w/v Brij 35 at pH=2.3±0.1. The potential potassium hydrogen sulfate screening concentrations were 0, 1.37, 2.75 and 8.0 mM. The solutions were mixed vigorously at room temperature for 15 seconds and then stored at 2-8° C. to induce DAB sulfate precipitation. Solutions were monitored for physical changes (i.e. color or precipitation). The candidate solutions were analyzed by HPLC before and after sulfate addition to confirm changes in DAB concentration relative to 2-hydroxypyridine as an internal standard. A summary of results are shown in Table 2 below.

Figure 14:
FIG. 14 is an image of a control slide wherein the tonsil tissue sample is stained for Ki67 with a DAB chromogen solution.
Figure 15:
FIG. 15 is an image of a tonsil tissue section stained for Ki67 with a DAB chromogen solution and 4 wt % polystyrene sulfonate (Mw=1.5 kDa).
Figure 16:
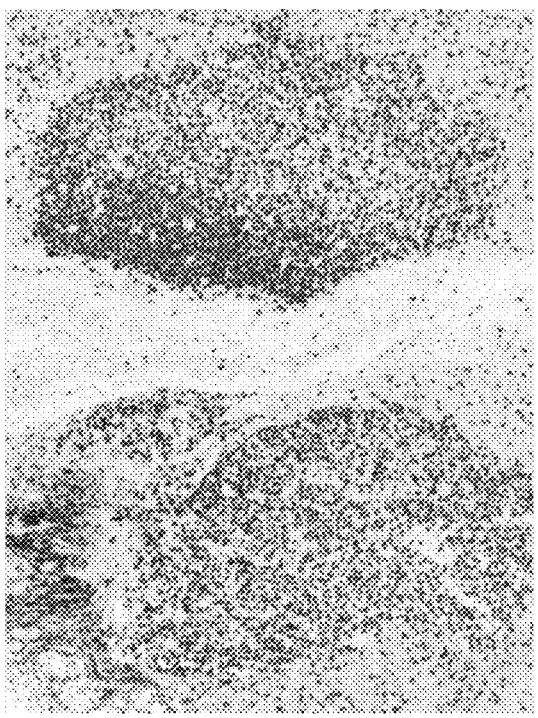
FIG. 16 is an image of a tonsil tissue section stained for Ki67 with a DAB chromogen solution and 4 wt % dextran sulfate (Mw=6.5-10 kDa).
Figure 17:
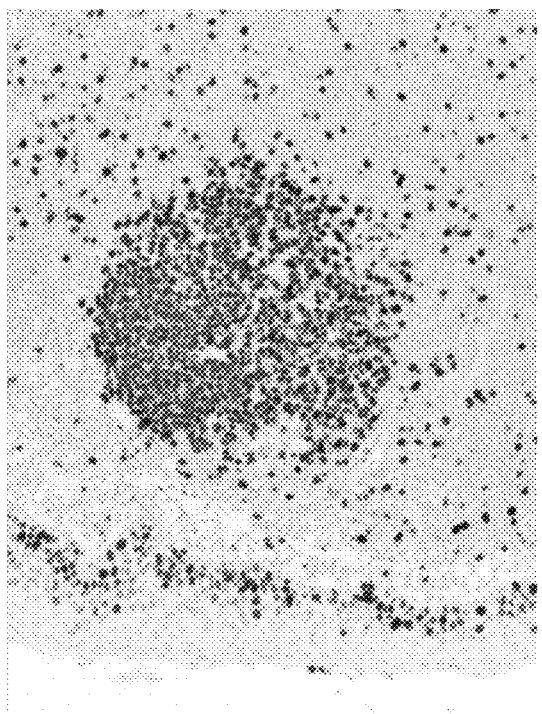
FIG. 17 is an image of a control slide wherein the tonsil tissue sample is stained for Ki67 with a DAB chromogen solution.
Figure 18:
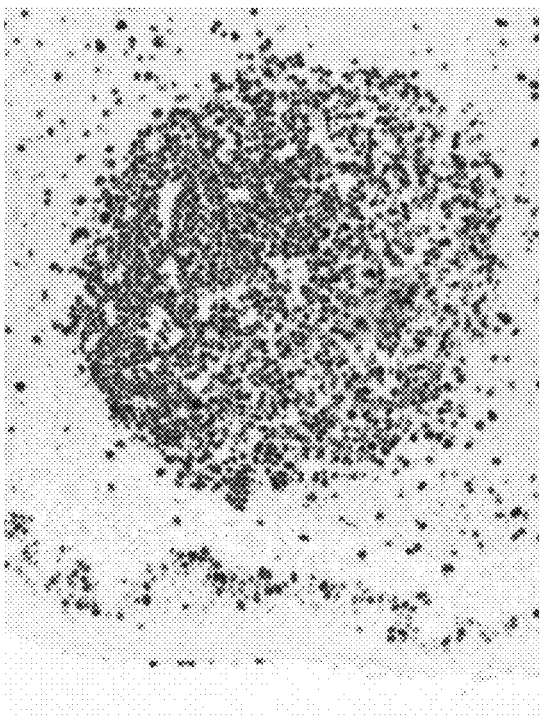
FIG. 18 is an image of a tonsil tissue section stained for Ki67 with a DAB chromogen solution and 5 wt % polyallylamine (Mw=15 kDa).
Figure 19:
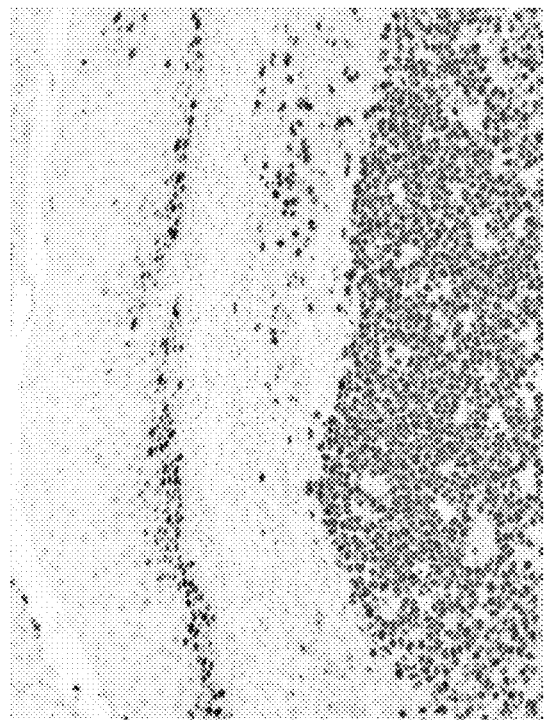
FIG. 19 is an image of a tonsil tissue sample stained for Ki67 with a solution of a DAB chromogen and 0.1 wt % of linear polyethyleneimine (Mw=2.5 kDa).
Figure 20:
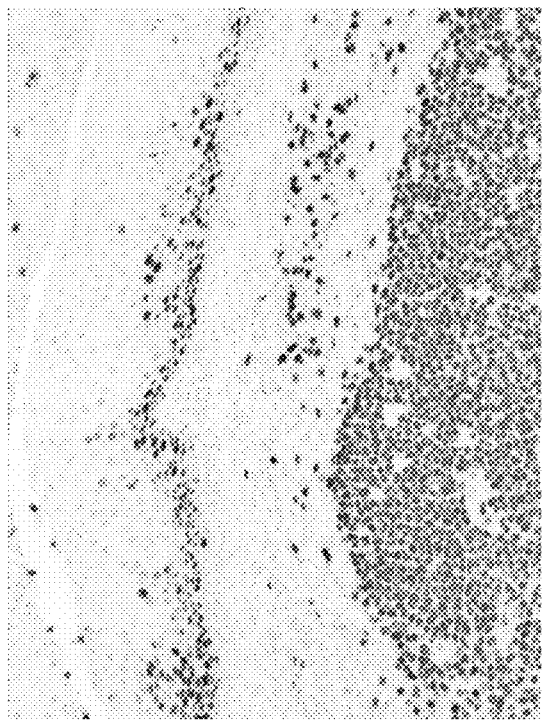
FIG. 20 is an image of a tonsil tissue sample stained for Ki67 with a solution of a DAB chromogen and 0.5 wt % of linear polyethyleneimine (Mw=2.5 kDa).
Figure 21:
FIG. 21 is an image of a tonsil tissue sample stained for Ki67 with a solution of a DAB chromogen and 1.0 wt % of linear polyethyleneimine (Mw=2.5 kDa).
Figure 22:
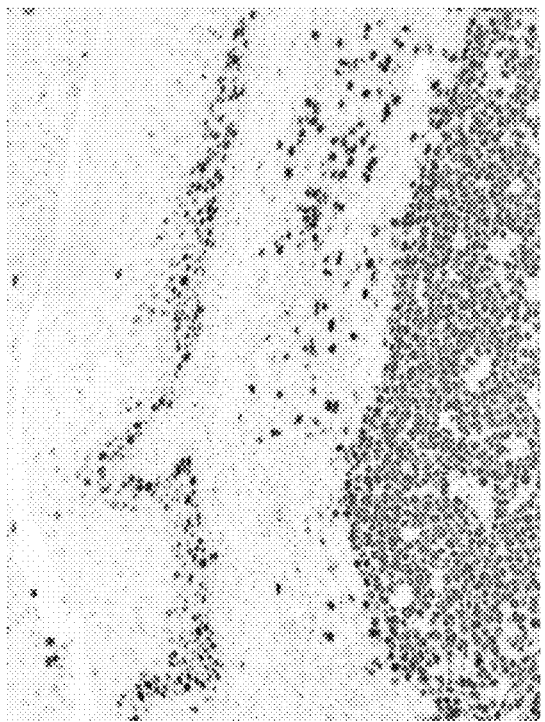
FIG. 22 is an image of a tonsil tissue sample stained for Ki67 with a solution of a DAB chromogen and 3.0 wt % of linear polyethyleneimine (Mw=2.5 kDa).

Exemplary polymers (dextran sulfate and polystyrene sulfonate) substantially inhibited DAB precipitation, and other exemplary polymers (dextran DEAE and 10 kDa aminodextran) also significantly reduced DAB precipitation. For example, FIGS. 14-16 collectively illustrate results obtained using exemplary sulfonate and sulfate polymers in comparison to a sampler wherein no polymer is used (FIG. 14). FIG. 15 is an image of a tissue section stained using the disclosed composition comprising the DAB solution and 4 wt % polystyrene sulfonate (1.5 kDa) and FIG. 16 is an image of a tissue section stained using the disclosed composition comprising the DAB solution and 4 wt % dextran sulfate (6.5-10 kDa). FIGS. 17 and 18 are images illustrating results obtained using a control (FIG. 17) and 5 wt % 15 kDa polyallylamine (FIG. 18). Further HPLC results of exemplary embodiments of the disclosed composition are summarized in Table 2.

TABLE 2

HPLC analytical data for candidate polymer stabilized DAB chromogen solutions treated with potassium hydrogen sulfate

| Enhanced DAB base (5.5 mM DAB) | 2.75 mM $KHSO_4$ | | 8.0 mM $KHSO_4$ | |
| --- | --- | --- | --- | --- |
| | DAB/2HP | % Δ | DAB/2HP | % Δ |
| Standard without $KHSO_4$ addition | 4.49 | | 4.49 | |
| Standard - No Polymer Added | 2.22 (b) | −50.6 | 0.40 (b) | −91.1 |
| PEG8000, 5 wt % | 2.40 (b) | −46.5 | n/d | n/d |
| 9-20 kDa Dextran Sulfate, 5 wt % | 4.07 | −9.4 | 3.66 | −18.5 |
| 6.5-10 kDa Dextran Sulfate, 5 wt % | 4.33 | −3.6 | 4.20 | −6.5 |
| 1.53 kDa Polystyrene Sulphonate, 5 wt % | 4.07 | −9.4 | 3.85 | −14.3 |
| 5.18 kDa Polystyrene Sulphonate, 5 wt % | 4.14 | −7.8 | 4.00 | −10.9 |
| 20 kDa Polystyrene Sulfonate Maleic Acid Co-polymer, 5 wt % | 4.10 | −8.7 | 4.00 | −10.9 |
| 2.5 kDa Linear polyethyleneimine (4 kDa HCl salt), 2 wt % | 4.50 | 0.0 | 4.49 | 0.0 |
| 2.5 kDa Linear polyethyleneimine (free base), 2 wt % | 4.51 | 0.0 | 4.56 | 0.0 |
| 1.8 kDa Branched Polyethyleneimine (free base), 2 wt % | 3.82 (a) | −14.9 | 3.82 (a) | −14.9 |
| 500 kDa Dextran DEAE, 7 wt % | 3.89 (a, b) | −13.4 | 1.08 (b) | −75.9 |
| 10 kDa Aminodextran, 5 wt % | 3.81 (a, b) | −15.1 | 0.68 (b) | −84.9 |
| Poly(2-vinyl-1-methylpyridinium bromide), 2 wt % | 4.25 (a) | −5.3 | 1.89 (a, b) | −57.9 |
| Poly(2-methylacryloxethyltrimethylammonium bromide), 2 wt % | 4.01 | −10.7 | 1.00 (a, b) | −77.7 |
| Poly(acrylamide/2-methylacryloxethyl-trimethylammonium bromide) (80:20), 2 wt % | 1.87 (b) | −58.3 | 0.30 (b) | −93.3 |

(a): New HPLC peak(s) present not yet identified,
(b): DAB sulfate precipitate observed HPLC analysis showed DAB solutions with and without PEG8000 both lost a similar amount of DAB from solution after addition of addition of 2.75 mM $KHSO_4$. Polyols and alcohols have been reported to reduce DAB sulfate precipitation. A non-volatile alcohol additive, such as 1,2-propanediol, failed to inhibit DAB sulfate precipitation. Dextran polymers reduced but did not completely inhibit DAB sulfate precipitation. Other polymer classes such as polyvinylalcohol (PVA), polyacrylamide (PAA), polyvinylpyrrolidinone (PVP), poly(propylene glycol) (PPG) were tested and failed to inhibit DAB sulfate precipitation.

Example 2

This particular example concerns using amine polymers in the disclosed composition. Amine polymers had a wide range of influence on DAB sulfate precipitate formation. Amine polymers are believed to form salts with the sulfate counteranion reducing frequency of DAB sulfate formation and/or help reduce the DAB sulfate particle size. DAB sulfate precipitation was not observed with DAB chromogen solutions containing linear polyethyleneimine (PEI), branched PEI or polyallylamine (PAA) polymers upon addition of either 2.75 or 8.0 mM $KHSO_4$. The influences of linear PEI polymer concentration (wt %) was examined in this process. A 2.5 kDa linear PEI was used as a 4 kDa HCl salt and varied from 0.1 to 5.0 wt % in the chromogen solution (see Table 3). The linear PEI inhibited DAB sulfate precipitation over the entire polymer concentration range at 2.75 mM $KHSO_4$. DAB sulfate precipitate was only observed with 8.0 mM $KHSO_4$ at 0.1 wt % PEI. Linear and branched PEI polymers were examined from 0.8 to 25 kDa in size. The polymer molecular weight did not change the polymer's effect on inhibiting DAB sulfate precipitation.

TABLE 3

HPLC analytical data for amine polymer stabilized DAB chromogen solutions treated with potassium hydrogen sulfate

| Enhanced DAB base (5.5 mM DAB) | 2.75 mM $KHSO_4$ DAB/2HP | % Δ | 8.0 mM $KHSO_4$ DAB/2HP | % Δ |
|---|---|---|---|---|
| Standard without $KHSO_4$ addition | 5.03 | | 5.03 | |
| 5 wt % Linear PEI (4 kDa HCl Salt) | 5.03 | 0.4 | 5.06 | 1.0 |
| 4 wt % Linear PEI (4 kDa HCl Salt) | 5.04 | 0.6 | 5.08 | 1.4 |
| 3 wt % Linear PEI (4 kDa HCl Salt) | 5.02 | 0.2 | 5.10 | 1.8 |
| 2 wt % Linear PEI (4 kDa HCl Salt) | 5.01 | 0.0 | 5.05 | 0.8 |
| 1 wt % Linear PEI (4 kDa HCl Salt) | 5.02 | 0.2 | 5.03 | 0.4 |
| 0.5 wt % Linear PEI (4 kDa HCl Salt) | 5.03 | 0.4 | 5.05 | 0.8 * |
| 0.1 wt % Linear PEI (4 kDa HCl Salt) | 5.04 | 0.6 * | 2.38 | −52.5 ** |

* A very minor haze was observed on bottom of vial, but no appreciable DAB sulfate ppt. formed.
** DAB sulfate precipitate was observed with extended storage at 4° C.

Aminodextran, dextran DEAE and quaternary amine polymers helped reduce, but did not completely inhibit, DAB sulfate precipitation. Amine polymer wt % concentration was important for these polymers. Higher concentrations of dextran DEAE were necessary to control the amount of DAB sulfate precipitation (see Table 4). The water solubility limit for dextran DEAE under formulation conditions did not allow for concentrations above 7 wt % of polymer to be examined.

TABLE 4

HPLC analytical data for 500 kDa dextran DEAE polymer stabilized DAB chromogen solutions treated with potassium hydrogen sulfate

| 500 kDa Dextran DEAE (5.5 mM DAB) | 2.75 mM $KHSO_4$ DAB/2HP | % Δ |
|---|---|---|
| Base no polymer or $KHSO_4$ | 4.49 | n/a |
| Base no polymer | 2.40 | −47 |
| 5 wt % PEG8000 | 2.40 | −47 |
| 3 wt % Dextran DEAE | 2.75 | −39 |
| 4 wt % Dextran DEAE | 2.94 | −35 |
| 5 wt % Dextran DEAE | 3.48 | −22 |
| 6 wt % Dextran DEAE | 3.43 | −24 |
| 7 wt % Dextran DEAE | 3.96 | −12 |

The influence of polymer concentration on DAB IHC staining was examined using an iView detection method (tonsil tissue, Ki67). A 2.5 kDa linear PEI was used as a 4 kDa HCl salt and varied from 0.1 to 5.0 wt % in the DAB chromogen solution. Representative images are shown at 20× (see FIGS. 19-22). More viscous DAB chromogen solutions reduced DAB IHC staining intensity and tissue coverage. Higher viscosity chromogen solutions are well known to reduce enzyme reaction rates in plate-based assays. Amine polymer solubility can be an issue at neutral pH in Ventana Reaction Buffer (i.e. 15 kDa polyallylamine,) which greatly affected the intensity and coverage of both DAB IHC and hematoxylin staining.

The influence of aminodextran polymer molecular weight on DAB IHC staining was examined using an iView detection method (tonsil tissue, Ki67). Aminodextran polymer-stabilized DAB chromogen solutions were prepared using 4 wt % of different molecular weight polymers. Representative images are shown at 10× (see FIGS. 9-12). DAB IHC staining intensity was not significantly affected by increasing polymer molecular weight. The aminodextran polymer was soluble in water and had no effect on solution viscosity at 4 wt %.

Figure 23:
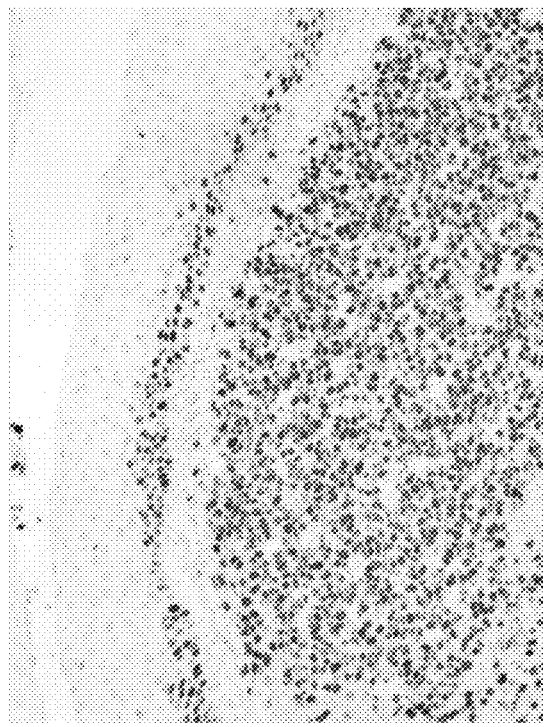
FIG. 23 is an image of a control slide wherein the tonsil tissue sample is stained for Ki67 with a solution of a DAB chromogen.
Figure 24:
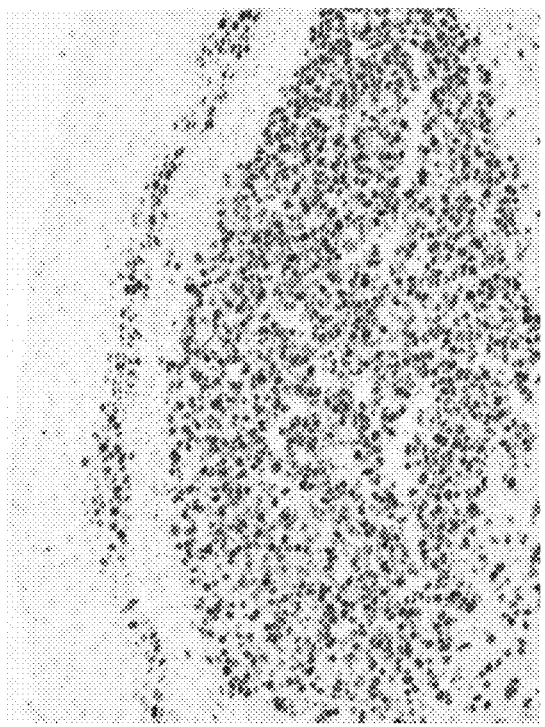
FIG. 24 is an image of a tonsil tissue sample stained for Ki67 with a solution of a DAB chromogen and 7 wt % of dextran DEAE (Mw=500 kDa).
Figure 25:
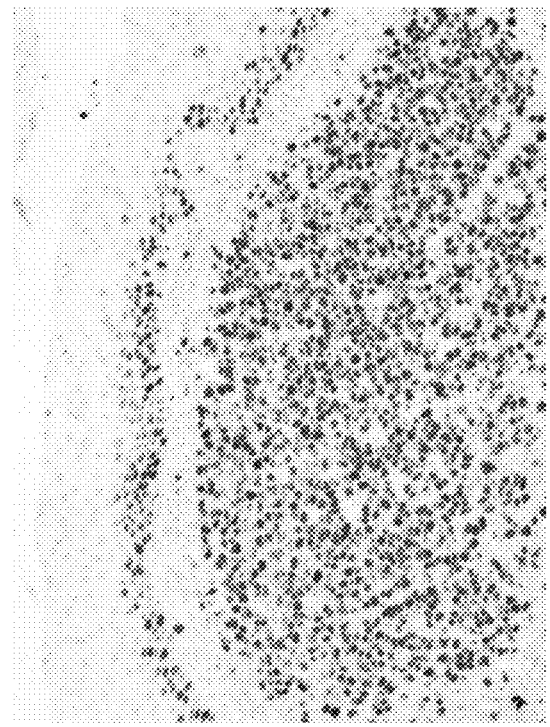
FIG. 25 is an image of a tonsil tissue sample stained for Ki67 with a solution of a DAB chromogen and 2 wt % of linear polyethyleneimine (Mw=2.5 kDa).

Amine polymer stabilized DAB chromogen solutions can be used without impacting DAB IHC tissue staining. Polymer wt % can be controlled to help inhibit DAB sulfate precipitation and control solution viscosity to reduce deleterious tissue staining effects. Exemplary working embodiments in this class include a 2.5 kDa linear PEI (2.5 kDa free base or 4 kDa HCl salt) and to a lesser extent 500 kDa dextran DEAE. Representative images are shown in FIGS. 23-25. These figures illustrate results of a tissue section stained with stabilized DAB chromogen solutions comprising no polymer (FIG. 23); 7 wt % 500 kDa dextran DEAE (FIG. 24); and 2 wt % 2.5 kDa linear PEI (FIG. 25). Dextran DEAE can have a minor influence on hematoxylin staining intensity, but it is much more subtle than observed with dextran sulfate.

Polymer stabilized DAB (OPTIVIEW® DAB solution) chromogen solutions were stained on tonsil tissue for Ki67 and CD10 antigen markers. Two different tissue blocks were examined for each antigen marker. Five serial section samples were stained for each condition. Each sample was evaluated by a qualified pathologist for DAB IHC staining intensity, IHC background, and hematoxylin counterstain quality. Each sample was compared to the commercially available DAB reagent without polymer (OPTIVIEW® DAB solution). A summary of the IHC staining results can be found in Table 5. No differences were observed for IHC background staining between chromogen samples. Subtle differences were observed in the hematoxylin counterstain between chromogen samples, but the counterstain hue and intensities were judged to be acceptable. The 2.5 kDa linear polyethylenimine free base and corresponding 4 kDa linear PEI HCl salt stained equivalently or better than the commercially available chromogen reagent on all samples except on Ki67 sample set. The 4 kDa linear PEI HCl salt stained slightly better than the 2.5 kDa linear PEI free base for CD10.

TABLE 5

IHC Detection of Ki67 and CD10 Antigens on Tonsil
using Polymer Stabilized DAB Chromogen Solutions

| | OptiView DAB IHC Staining Intensity (Ki67, Tonsil) | | | | OptiView DAB IHC Staining Intensity (CD10, Tonsil) | | | |
|---|---|---|---|---|---|---|---|---|
| | Tissue Block 352-10-23 | | Tissue Block 397-10-12 | | Tissue Block 357-10-10 | | Tissue Block 386-10-7 | |
| DAB + Polymer Stabilizer | ave. score | std. dev. | ave. score | std. dev. | ave. score | std. dev. | ave. score | std. dev. |
| A. Commercially available DAB | 2.4 | 0.5 | 3.0 | 0.0 | 1.8 | 0.4 | 1.6 | 0.5 |
| B. A with no PEG or stannate | 2.4 | 0.5 | 3.0 | 0.0 | 1.4 | 0.9 | 1.8 | 0.4 |
| B. with 0.15 wt % linear PEI (4 kDa HCl salt) | 2.2 | 0.4 | 3.0 | 0.0 | 2.0 | 0.0 | 2.0 | 0.0 |
| B. with 0.15 wt % Linear PEI (2.5 kDa free base) | 2.2 | 0.4 | 3.0 | 0.0 | 1.8 | 0.4 | 1.8 | 0.4 |
| B. with 2.0 wt % Dextran Sulfate (6.5-10 kDa) | 1.8 | 0.4 | 2.0 | 0.0 | 1.4 | 0.5 | 1.4 | 0.5 |
| B. with 2.0 wt % Polystyrenesulfonate (1 kDa) | 2.8 | 0.4 | 2.6 | 0.5 | 1.2 | 0.4 | 1.0 | 0.0 |
| B. with 7.0 wt % Dextran DEAE (500 kDa) | 1.1 | 0.5 | 2.0 | 0.7 | 1.4 | 0.5 | 1.0 | 0.5 |

The amine polymer stabilized DAB chromogen solutions were thermally stressed at 45° C. to examine chromogen stability in the presence of the new polymers. DAB chromogen solutions stabilized with 4 kDa linear PEI HCl salt polymer (2.5 kDa free base equiv.) demonstrated the greatest chromogen stability (see Table 6 and 7) for those polymers tested. DAB Chromogen solutions with ≤1 wt % 4 kDa linear PEI HCl salt polymer demonstrated stability greater than the base chromogen solution. DAB Chromogen solutions with 2.5 kDa linear PEI free base polymer demonstrated similar stability to the base chromogen solution. Branched PEI, dextran DEAE and 4° C. amine polymers formed byproducts with DAB decreasing chromogen stability. These byproducts were not isolated or confirmed by structural analysis.

TABLE 6

HPLC analytical data for polymer stabilized DAB chromogen solutions thermally stressed at 45° C.

| | 1 d-45° C. | | 4 d-45° C. | | 10 d-45° C. | | 24 d-45° C. | |
|---|---|---|---|---|---|---|---|---|
| DAB base + Polymer | DAB / 2 HP | % Δ | DAB / 2 HP | % Δ | DAB / 2 HP | % Δ | DAB / 2 HP | % Δ |
| No Polymer Standard | 4.89 | −2.4 | 4.82 | −3.8 | 4.73 | −5.6 | 3.81 | −24 |
| 5 wt % Linear PEI (4 kDa HCl Salt) | 4.91 | −2.0 | 4.95 | −1.2 | 4.64 | −7.4 | 3.90 | −22 |
| 4 wt % Linear PEI (4 kDa HCl Salt) | 4.90 | −2.2 | 4.95 | −1.2 | 4.68 | −6.6 | 3.97 | −21 |
| 3 wt % Linear PEI (4 kDa HCl Salt) | −3.0 | 4.86 | 4.97 | −0.8 | 4.72 | −5.8 | 3.70 | −26 |
| 1 wt % Linear PEI (4 kDa HCl Salt) | 5.00 | −0.2 | 4.97 | −0.8 | 4.69 | −6.4 | 4.31 | −14 |
| 0.5 wt % Linear PEI (4 kDa HCl Salt) | 5.01 | 0.0 | 5.02 | 0.2 | 4.77 | −4.8 | 4.35 | −13 |
| 0.1 wt % Linear PEI (4 kDa HCl Salt) | 5.00 | −0.2 | 5.02 | 0.2 | 4.77 | −4.8 | 4.77 | −4.8 |
| 5 wt % Branched PEI (25 kDa HCl Salt) | 2.29 | −54** | 2.32 | −54** | 0.82 | −84** | n/a | n/a |

TABLE 6-continued

HPLC analytical data for polymer stabilized DAB chromogen solutions thermally stressed at 45° C.

| DAB base + Polymer | 1 d-45° C. | | 4 d-45° C. | | 10 d-45° C. | | 24 d-45° C. | |
|---|---|---|---|---|---|---|---|---|
| | $\frac{DAB}{2\ HP}$ | % Δ | $\frac{DAB}{2\ HP}$ | % Δ | $\frac{DAB}{2\ HP}$ | % Δ | $\frac{DAB}{2\ HP}$ | % Δ |
| 4 wt % Branched PEI (25 kDa HCl Salt) | 2.66 | −47** | 2.65 | −47** | 1.53 | −69** | n/a | n/a |
| 3 wt % Branched PEI (25 kDa HCl Salt) | 2.99 | −40** | 3.01 | −40** | 2.05 | −59** | n/a | n/a |
| 2 wt % Branched PEI (25 kDa HCl Salt) | 3.26 | −35** | 3.30 | −34** | 2.70 | 46** | n/a | n/a |
| 7 wt % Dextran DEAE (500 kDa) | 4.61 | −8.0** | 4.51 | −10** | 4.01 | −20** | 2.45 | −51** |

**New HPLC byproduct peak(s) were present in chromogen solution.

TABLE 7

HPLC analytical data for polymer stabilized DAB chromogen solutions thermally stressed at 45° C.

| DAB base + 2 wt % Polymer | 1 d-45° C. | | 3 d-45° C. | | 9 d-45° C. | | 23 d-45° C. | |
|---|---|---|---|---|---|---|---|---|
| | $\frac{DAB}{2\ HP}$ | % Δ | $\frac{DAB}{2\ HP}$ | % Δ | $\frac{DAB}{2\ HP}$ | % Δ | $\frac{DAB}{2\ HP}$ | % Δ |
| No Polymer Control | 4.91 | −2.0 | 4.82 | −3.8 | 4.66 | −7.0 | 3.66 | −26.9 |
| Poly(2-vinyl-1-methylpyridinium bromide) | 4.08 | −19** | 3.70 | −26** | 2.42 | −52** | n.d. | −100** |
| Poly(acrylamide/2-methylacryloxethyl-trimethyl-ammonium bromide) (80:20) | 4.71 | −6.0** | 4.50 | −10** | 4.33 | −14** | 3.92 | −22** |
| Poly(2-methylacrylox-ethyltrimethyl-ammonium bromide) | 4.53 | −9.6** | 4.34 | −13** | 4.14 | −17** | 2.15 | −57** |
| Branched PEI Low MW (2.0 kDa HCl Salt) | 3.21 | −36** | 3.20 | −36** | 2.98 | −41** | 1.26 | −75** |
| Branched PEI (1.3 kDa HCl Salt) | 3.37 | −33** | 3.37 | −33** | 3.29 | −34** | 2.27 | −55** |
| Branched PEI (1.8 kDa HCl Salt) | 3.42 | −32** | 3.01 | −40** | 1.21 | −76** | n.d. | −100** |
| Linear PEI (2.5 kDa free amine polymer) | 4.97 | −0.8 | 4.89 | −2.4 | 4.71 | −6.0 | 3.60 | −28.1 |

**New HPLC byproduct peak(s) were present in chromogen solution.

DAB sulfate precipitation was not observed with DAB chromogen solutions containing linear polyethyleneimine (PEI), branched PEI or polyallylamine (PAA) polymers upon addition of either 2.75 or 8.0 mM KHSO₄. Branched PEI polymers appear to react with DAB forming byproducts observed in HPLC analysis. Aminodextran, dextran DEAE and quaternary amine polymers reduced but did not completely inhibit DAB sulfate precipitation. New DAB-polymers byproducts were observed during HPLC analysis with aminodextran and 4° amine polymers. The proposed DAB-polymer byproducts were not isolated or confirmed by structural analysis. Small monomeric like amine materials, namely amino acids or ethanolamines (mono-, di- and tri-), did not inhibit DAB sulfate precipitation.

Example 3

This example concerns particular embodiments of the disclosed composition and sulfate and/or sulfonate polymers. Sulfate and sulfonate polymers are believed to form a DAB-polymer salt complex where the hydrophilic polymer backbone helps maintain water solubility. The OptiView DAB chromogen solutions were prepared with variable dextran sulfate (9-29 kDa) polymer concentrations (0.25 to 5 wt %). A precipitate was observed with the OptiView DAB chromogen solutions containing less than 1 wt % dextran sulfate polymer (9-29 kDa). A higher DAB-to-polymer ratio occurred with lower wt % dextran sulfate polymer solutions, which increased the DAB-polymer complex hydrophobicity and caused it to lose water solubility. No DAB sulfate precipitate was observed with the OptiView DAB chromogen solutions with greater then 2 wt % dextran sulfate (9-29 kDa) upon addition of either 2.75 or 8.0 mM $KHSO_4$. A similar effect was observed with different molecular weight sized polystyrene sulfonate (PSS) polymers. Smaller PSS polymers, such as 1.5 or 3.1 kDa PSS, were more prone to low DAB-polymer complex solubility at lower wt % polymer concentrations than their larger molecular weight PSS polymers. Dextran sulfate polymers under 6 kDa molecular weight were also prone to lower DAB-polymer complex solubility.

The influence of PSS polymer molecular weight on DAB IHC staining was examined using an iView detection method (tonsil tissue, Ki67). PSS polymer stabilized DAB chromogen solutions were prepared using different molecular weight PSS at 2 wt %. Representative images are shown at 10× in FIGS. 3-8. FIG. 3 illustrates results from a tissue section stained with an OptiView DAB chromogen solution. FIG. 4-FIG. 8 illustrates results from a tissue section stained with a 4 wt % polystyrene sulfonate (1.5 kDa, 5.1 kDa, 7.5 weight dextran sulfate (6-9.5 kDa) and polystyrene sulfonate (molecular weight=1.53 kDa, Mn=1.37 kDa). Representative images are shown in FIGS. 14-16. These figures illustrate results of a tissue section stained with stabilized DAB chromogen solutions comprising no polymer (FIG. 14); 4 wt % 1.53 kDa polystyrene sulfonate (FIG. 15); and 4 wt % 6.5-10 kDa dextran sulfate (FIG. 16).

The sulfate and sulfonate polymer-stabilized DAB chromogen solutions were thermally stressed at 45° C. to examine chromogen stability in the presence of the new polymers. As previously stated, higher molecular weight PSS polymers are used in water purification for sequestering polyvalent metals. Polyvalent metal contaminants are known to catalyze DAB oxidation. Sulfate and sulfonate polymers may contain potential polyvalent metal contaminants and result faster DAB oxidation rates. Dextran sulfates, PSS and PSSMA polymers have demonstrated the ability to cause lower DAB chromogen stability (see Table 8). Dextran sulfate and PSSMA polymers were prone to forming DAB byproducts which were observed during HPLC analysis. These byproducts were not isolated or confirmed by structural analysis. Polystyrene sulfonate (PSS) polymers contained variable amounts of contaminants, which effect DAB oxidation rates. The PSS stabilized DAB chromogen solutions were as stable as the base solution in certain cases.

TABLE 8

HPLC analytical data for polymer stabilized DAB chromogen solutions thermally stressed at 45° C.

| | 1 d-0° C. | | 5 d-0° C. | | 25 d-0° C. | |
|---|---|---|---|---|---|---|
| DAB base + 5 wt % Polymer | $\frac{DAB}{2\,HP}$ | % Δ | $\frac{DAB}{2\,HP}$ | % Δ | $\frac{DAB}{2\,HP}$ | % Δ |
| No Polymer Standard | 4.60 | n/a | 4.57 | −0.7 | 3.10 | −33 |
| 9-20 kDa Dextran Sulfate | 4.15 | −9.8 | 2.13 | −53** | n/a† | 100** |
| 6.5-10 kDa Dextran Sulfate | 4.58 | −0.4 | 3.92 | −15** | 0.45 | −90** |
| 1.53 kDa PSS | 4.07 | −12 | 3.70 | −20 | 1.27 | −72 |
| 5.18 kDa PSS | 4.28 | −7.0 | 4.10 | −11 | 3.01 | −35 |
| 15 kDa PSS Maleic Acid Co-polymer | 4.04 | −12.2 | 2.31 | −49** | n/a | n/a |
| Low MW PSS Maleic Acid Co-polymer | 4.15 | −9.8 | 2.61 | −43** | n/a | n/a |

**New HPLC byproduct peak(s) were present in chromogen solution.
†No DAB remaining.

kDa, 16 kDa, and 35 kDa, respectively) stabilized DAB chromogen solutions. DAB IHC staining intensity and coverage decreased with increasing PSS molecular weight. The net apparent DAB-PSS polymer complex molarity decreases with increased polymer molecular weight. A lower DAB concentration has been shown to cause the observed effects. The hematoxylin counterstain intensity and background increased with increased polymer molecular weight. Hematoxylin counterstain intensity and background are controlled by tissue pH during counterstain application. The DAB-PSS polymer complex deposited on tissue will be deprotonated in Ventana Reaction Buffer and require further pH adjustment during counterstaining. Polystyrene sulfonate maleic acid (PSSMA) co-polymers were not found under 15 kDa molecular weight to provide appropriate DAB IHC staining.

Sulfate and sulfonate polymers do have some subtle impact on DAB tissue staining; however, this impact can be largely controlled with polymer size and concentration. DAB tissue staining was reduced and hematoxylin background staining increased with larger polymers. Polymer wt % provided less impact on tissue staining with smaller polymers; however, optimization was required for polymer complex solubility and DAB sulfate precipitate prevention. Top polymer candidates in this class were low molecular In summary, higher molecular weight polystyrene sulfonate (PSS) polymers are used in water purification for sequestering polyvalent metals. Polyvalent metal contaminants increase DAB oxidation rates. Dextran sulfates, polystyrene sulfonates and polystyrene sulfonate maleic acid (PSSMA) polymers were leading polymers candidates in this group to reduce DAB sulfate precipitation. Polyvinylsufonic acid (4-6 kDa PVS, Na salt) and polyethylene glycol sulfate (600 Da) did not form a water soluble DAB-polymer complex. Small sulfate monomeric-like materials, namely 2-aminoethylhydrogen sulfate, did not form water soluble DAB complexes.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A composition for chromogenic immunohistochemistry comprising in a solution:
   a solvent; 3,3'-diaminobenzidine or a derivative thereof; a stabilizer, and a polymer soluble in the solvent, wherein the polymer soluble in the solvent is polyethyleneimine, and wherein the polyethyleneimine has a molecular weight ranging from 0.8 kDa to 25 kDa.

2. The composition of claim 1, wherein the polymer soluble in the solvent is present in the composition in amount ranging from between about 0.05% to about 10% by total weight of the composition.

3. The composition of claim 1, wherein the stabilizer is selected from the group consisting of is sodium metabisulfite and sodium bisulfite.

4. The composition of claim 1, wherein the stabilizer comprises sodium stannate or a salt or hydrate thereof.

5. The composition of claim 1, further comprising an enhancer selected from the group consisting of imidazole, 2-hydroxypyridine, and combinations thereof.

6. The composition of claim 1, wherein the stabilizer is selected from the group consisting of is sodium metabisulfite, sodium bisulfite, sodium stannate, a hydrate of sodium stannate, and combinations thereof; and wherein the polymer soluble in the solvent is polyethyleneimine.

7. The composition of claim 6, further comprising an enhancer selected from the group consisting of imidazole, 2-hydroxypyridine, and combinations thereof.

8. The composition of claim 1, wherein the polyethyleneimine is linear polyethyleneimine.

9. The composition of claim 1, wherein the polyethyleneimine is branched polyethyleneimine.

10. The composition of claim 1, wherein the polyethyleneimine is a polyethyleneimine salt.

11. The composition of claim 10, wherein the polyethyleneimine salt is a polyethyleneimine HCl salt.

12. The composition of claim 10, wherein the polyethyleneimine salt has a molecular weight of about 4 kDa.

13. The composition of claim 1, wherein the molecular weight of the polyethyleneimine is about 2.5 kDa.

14. The composition of claim 1, wherein the polyethyleneimine is a polyethyleneimine free amine having a molecular weight of about 2.5 kDA.

15. The composition of claim 1, wherein the polyethyleneimine is a polyethyleneimine HCl salt having a molecular weight of about 4 kDA.

16. A composition for chromogenic immunohistochemistry comprising in a solution:
   a solvent; 3,3'-diaminobenzidine; a stabilizer, and a polymer soluble in the solvent, wherein the polymer soluble in the solvent is selected from the group consisting of a polystyrene sulfonate polymer having a molecular weight ranging from about 1 kDa to about 40 kDa and a polystyrene/maleic acid co-polymer having a molecular weight of about 20 kDa;
   wherein an amount of the polymer soluble in the solvent ranges from between about 2 wt % to about 5 wt % by total weight of the composition.

17. The composition of claim 16, wherein the stabilizer is selected from the group consisting of is sodium metabisulfite and sodium bisulfite.

* * * * *